US009638671B2

(12) United States Patent
Borigo et al.

(10) Patent No.: US 9,638,671 B2
(45) Date of Patent: May 2, 2017

(54) SYSTEMS AND METHODS FOR DAMAGE DETECTION IN STRUCTURES USING GUIDED WAVE PHASED ARRAYS

(71) Applicant: FBS, Inc., Bellefonte, PA (US)

(72) Inventors: Cody Borigo, Pennsylvania Furnace, PA (US); Steven E. Owens, Bellefonte, PA (US); Joseph L. Rose, State College, PA (US)

(73) Assignee: FBS, Inc., Bellefonte, PA (US)

( * ) Notice: Subject to any disclaimer, the term of this patent is extended or adjusted under 35 U.S.C. 154(b) by 225 days.

(21) Appl. No.: 14/532,766

(22) Filed: Nov. 4, 2014

(65) Prior Publication Data

US 2015/0073729 A1    Mar. 12, 2015

Related U.S. Application Data

(63) Continuation-in-part of application No. 13/901,786, filed on May 24, 2013, now abandoned.
(Continued)

(51) Int. Cl.
  *G01N 29/06* (2006.01)
  *G01N 29/07* (2006.01)
(Continued)

(52) U.S. Cl.
  CPC ....... *G01N 29/069* (2013.01); *G01N 29/0672* (2013.01); *G01N 29/07* (2013.01);
(Continued)

(58) Field of Classification Search
  CPC .. G01N 29/041; G01N 29/043; G01N 29/221; G01N 29/223; G01N 29/225;
(Continued)

(56) References Cited

U.S. PATENT DOCUMENTS 5,473,245 A * 12/1995 Silvus, Jr. ............... G01B 7/02
                                                          310/333
5,715,498 A *  2/1998 Takeuchi ............... H04N 1/047
                                                          399/301
(Continued)

OTHER PUBLICATIONS

Roger et al. (Large Area Corrosion Detection in Complex Aircraft Components using Lamb Wave Tomography, 6th International Workshop 2007).*
(Continued)

*Primary Examiner* — Michael A Lyons
*Assistant Examiner* — Suman K Nath
(74) *Attorney, Agent, or Firm* — Duane Morris LLP

(57) ABSTRACT

A method for ultrasonic guided wave defect detection in a structure is disclosed. The method includes driving a plurality of transducers to cause guided waves to be transmitted in the structure in a predetermined direction or focused at a predetermined focal point, receiving at least one reflected guided wave signal, and generating image data of the structure based on the at least one reflected guided wave signal. Processed image data are generated by performing at least one of baseline image subtraction or image suppression on the image data, and a location of at least one possible defect in the structure is identified based on the processed image data.

16 Claims, 28 Drawing Sheets

Related U.S. Application Data

(60) Provisional application No. 61/651,864, filed on May 25, 2012.

(51) Int. Cl.
*G01N 29/34* (2006.01)
*G01N 29/24* (2006.01)
*G01N 29/26* (2006.01)
*G01N 29/11* (2006.01)

(52) U.S. Cl.
CPC ......... *G01N 29/11* (2013.01); *G01N 29/2412* (2013.01); *G01N 29/262* (2013.01); *G01N 29/343* (2013.01); *G01N 29/348* (2013.01); *G01N 2291/044* (2013.01); *G01N 2291/0425* (2013.01); *G01N 2291/2632* (2013.01)

(58) Field of Classification Search
CPC ............. G01N 29/2437; G01N 29/245; G01N 29/2487; G01N 29/26; G01N 29/265; G01N 2291/0422
USPC .......................................... 73/628, 644, 641
See application file for complete search history.

(56) References Cited

U.S. PATENT DOCUMENTS

| | | | |
|---|---|---|---|
| 6,396,262 B2* | 5/2002 | Light .................. | G01N 17/006 324/220 |
| 2007/0008820 A1* | 1/2007 | Yang .................. | G01S 7/52004 367/99 |
| 2008/0289423 A1* | 11/2008 | Gordon ............... | G01N 29/069 73/602 |
| 2009/0047921 A1* | 2/2009 | Hayashi .................. | H03D 7/18 455/308 |
| 2010/0217544 A1* | 8/2010 | Yan ........................ | G01N 29/07 702/56 |
| 2011/0054806 A1* | 3/2011 | Goldfine .................. | G07C 3/00 702/34 |

OTHER PUBLICATIONS

Trindade et al. (Finite element homogenization technique for the characterization of d15 shear piezoelectric macro-fibre composites, Smart Materials and Structures 20 (2011) 075012 (17pp)).*

Yan et al. (Journal of Intelligent Material Systems and Structures, vol. 21—Feb. 2010, p. 377-384).*

Giurgiutiu, V. (Apr. 2005), "Tuned Lamb Wave Excitation and Detection with Piezoelectric Wafer Active Sensors for Structural Health Monitoring," J. Intel. Mat. Sys. Struct. 16, 291-305.

Purekar, A.S., Pines, D.J., Sundararaman, S. and Adams, D.E. (1994), "Directional Piezoelectric Phased Array Filters for Detecting Damage in Isotropic Plates," Smart Mater. Struct. 13, 838-850.

Wilcox, P.D. (Jun. 2003), "Omni-Directional Guided Wave Transducer Arrays for the Rapid Inspection of Large Areas of Plate Structures," IEEE Trans. Ultrason., Ferroelect., Freq. 50(6), 699-709.

Fromme, P., Wilcox, P.D., Lowe, M.J.S., and Cawley, P. (Apr. 2006), "On the Development and Testing of a Guided Ultrasonic Wave Array for Structural Integrity Monitoring," Trans. Ultrason., Ferroelect., Freq. 53(4): 777-785.

Gao, H., Yan, F., Rose, J.L., Zhao, X., Kwan, C. and Agarwala, V. (2005), "Ultrasonic guided wave tomography in structural health monitoring of an aging aircraft wing," Conference Proceeding of ASNT Fall Conference, Columbus, OH, Oct. 17-21, 2005: 412-415.

Royer, R.L. Jr., Zhao, X, Owens, S.E., and Rose, J.L. (2007), "Large Area Corrosion Detection in Complex Aircraft Components using Lamb Wave Tomography," Proceedings, 6th International Workshop on Structural Health Monitoring, Sep. 11-13, 2007, 238-246.

Ihn, J.B. and Chang, F-K (2004), "Detection and Monitoring of Hidden Fatigue Crack Growth Using a Built-in Piezoelectric Sensor/Actuator Network: II. Validation Using Riveted Joints and Repair Patches," Smart Mater. Struct. 13, 621-630.

Yan, F., "Ultrasonic guided wave phased array for isotropic and anisotropic plates", The Pennsylvania State Ph.D. Thesis, (Dec. 2008).

Berik, P. et al., (Sep. 6, 2010), "Piezoelectric d15 shear response-based torsion actuation mechanism: an experimental benchmark and its 3D finite element simulation", Int. J. Smart Nano Mat., 1(3), 224-235.

* cited by examiner

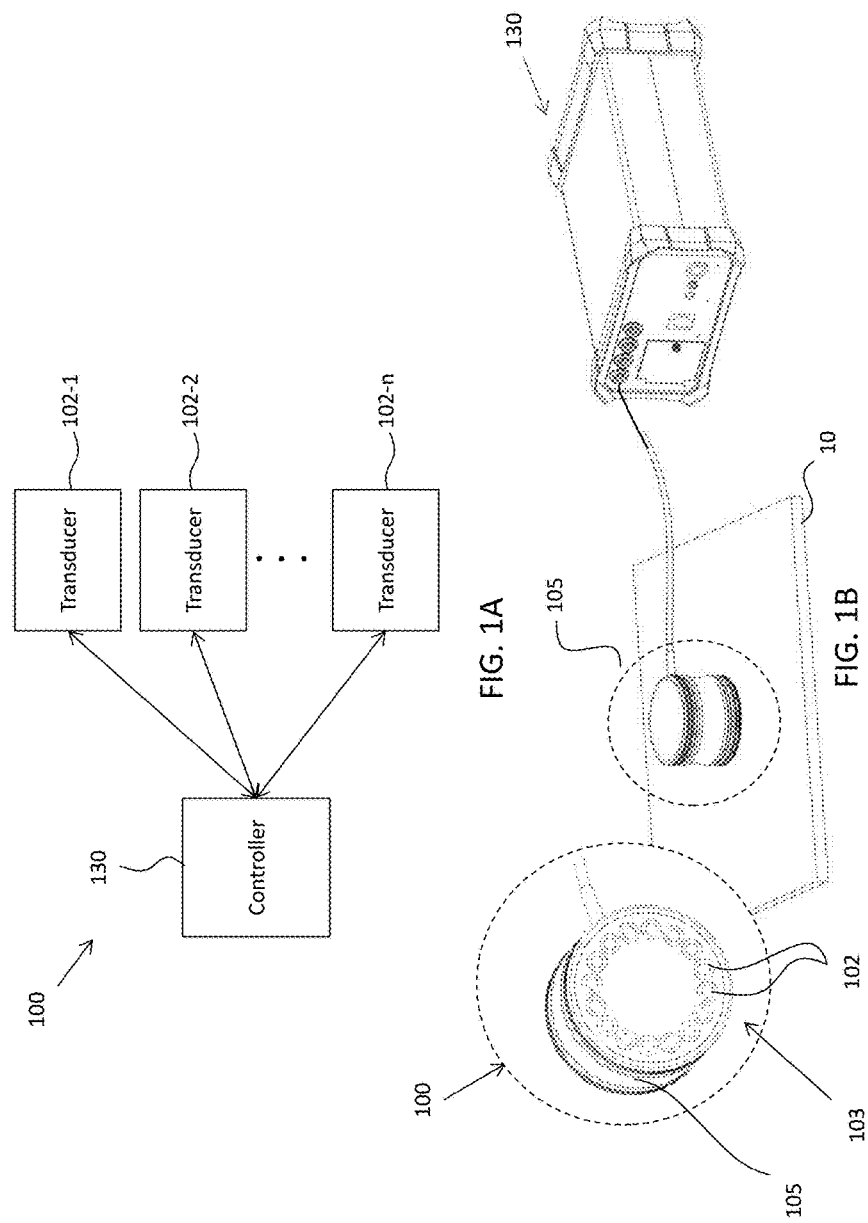

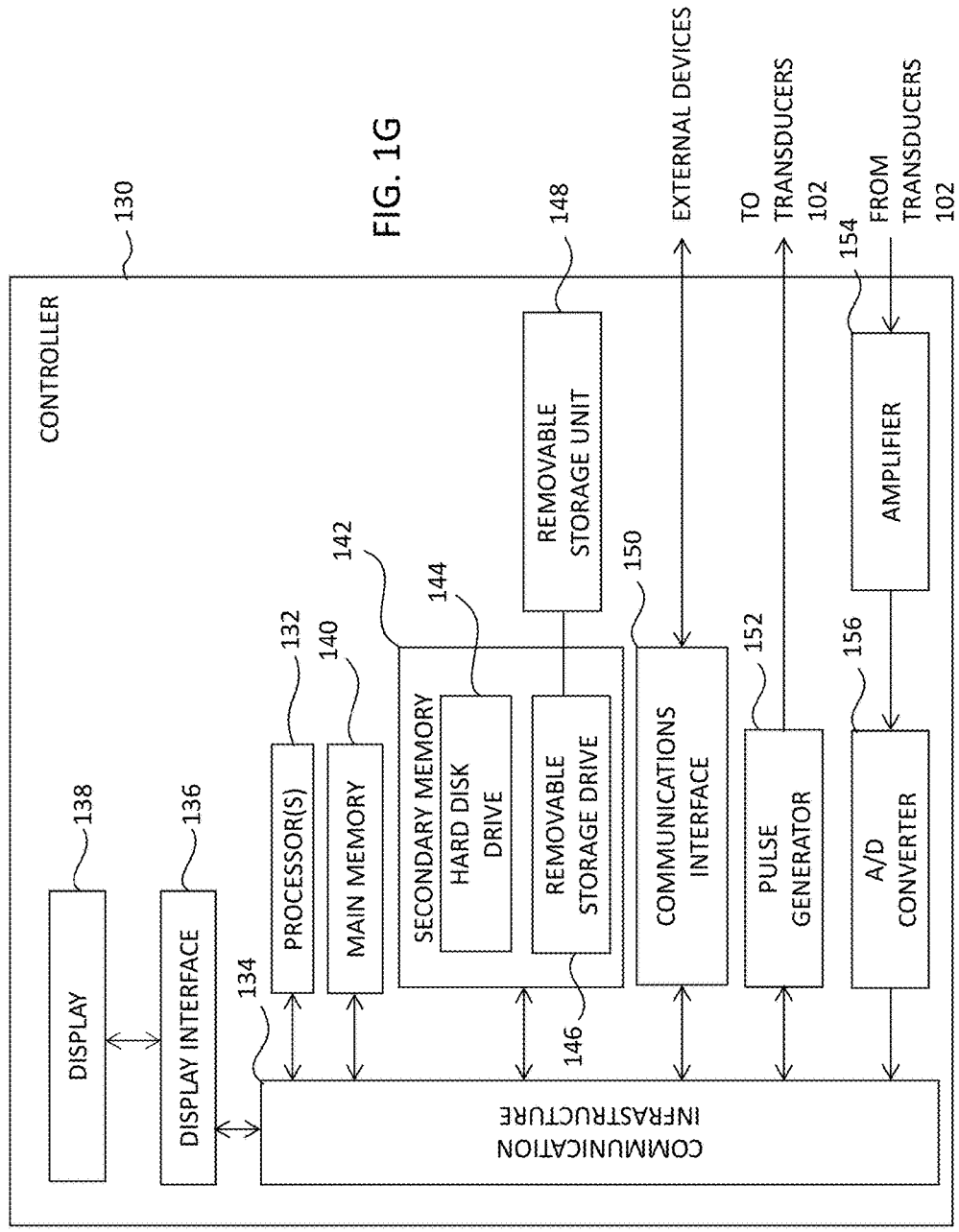

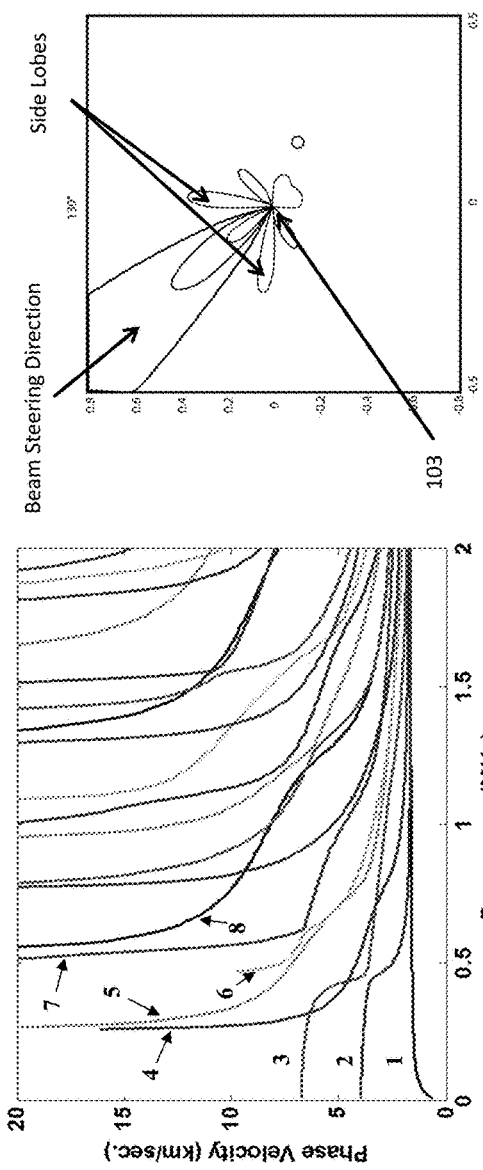

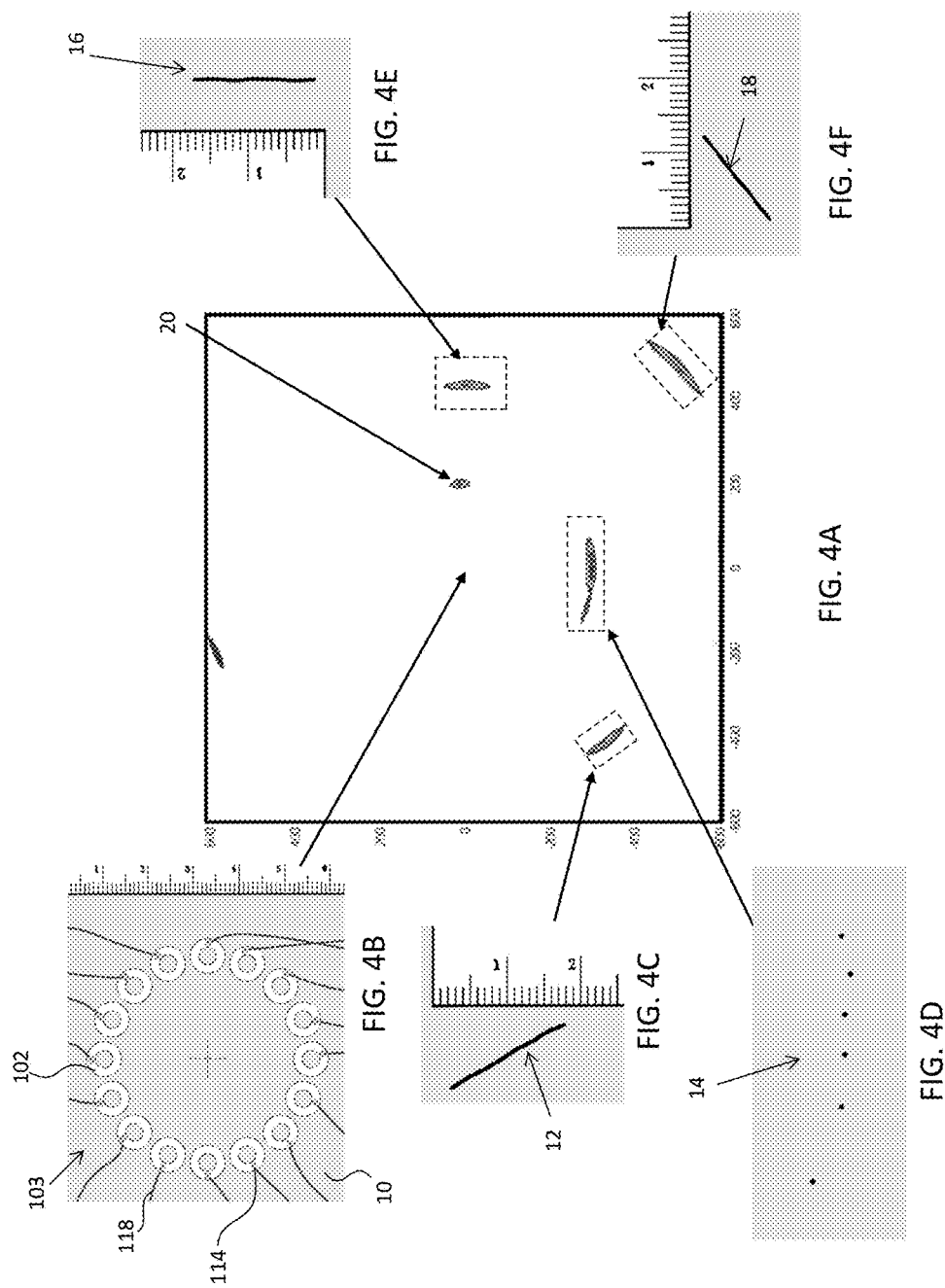

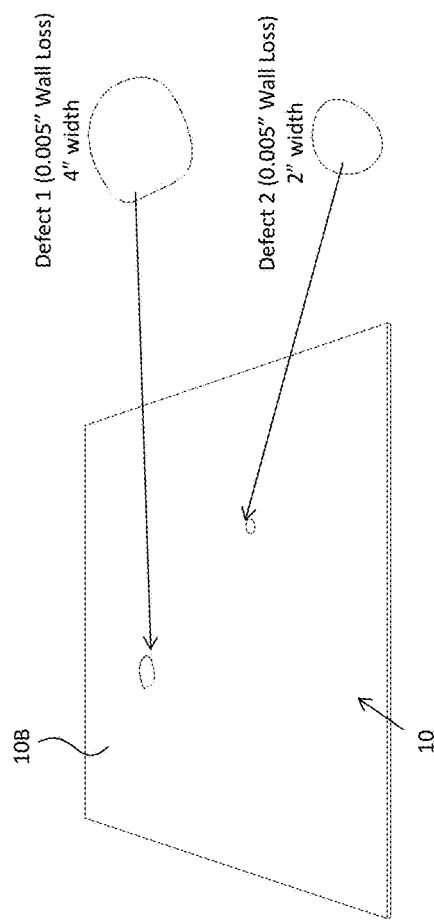
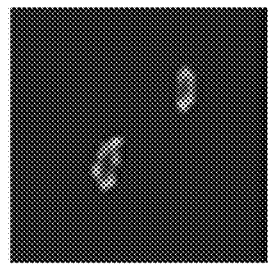
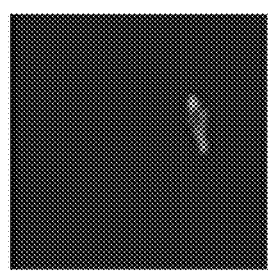
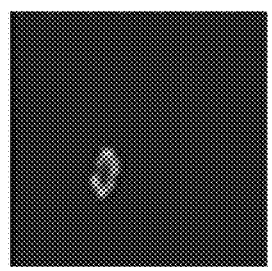
FIG. 6B
FIG. 7A  FIG. 7B  FIG. 7C

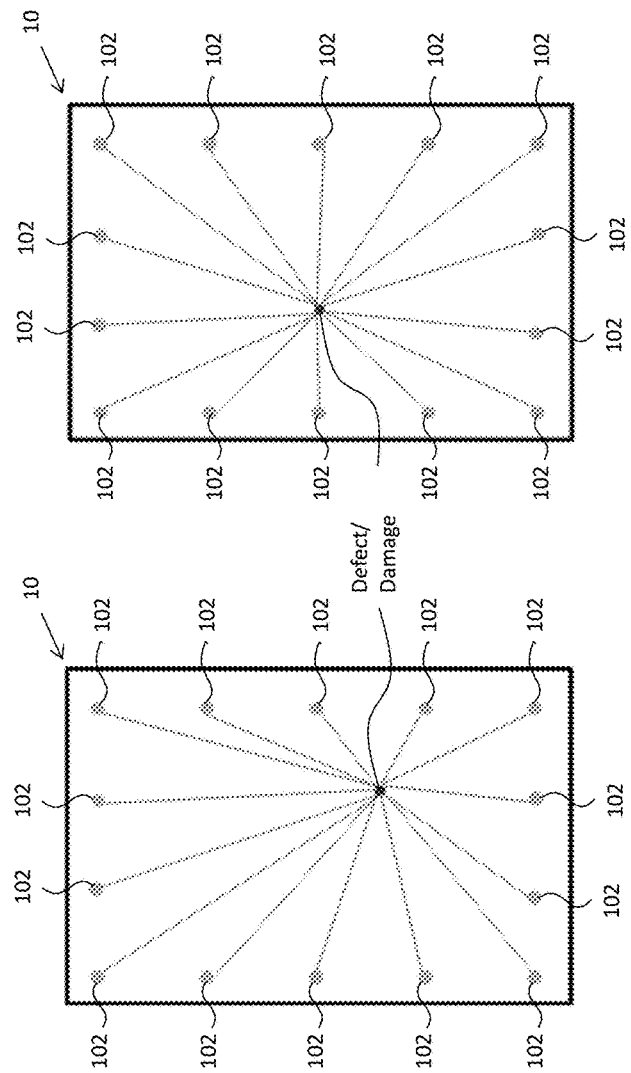

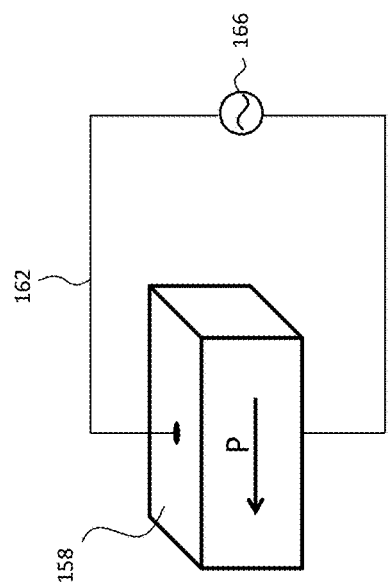
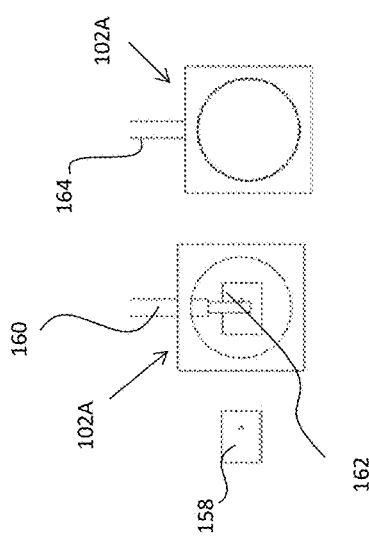
FIG. 10A
FIG. 10B

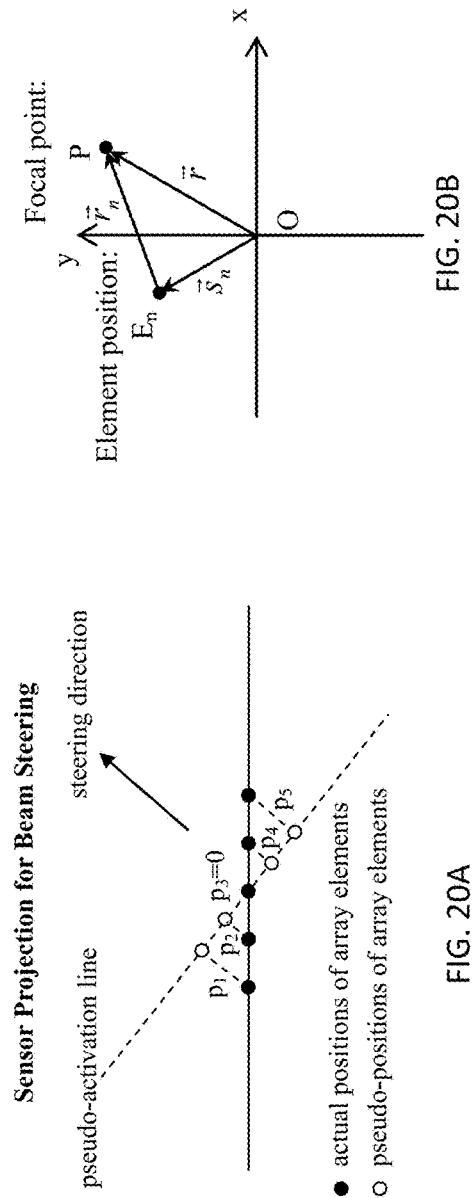

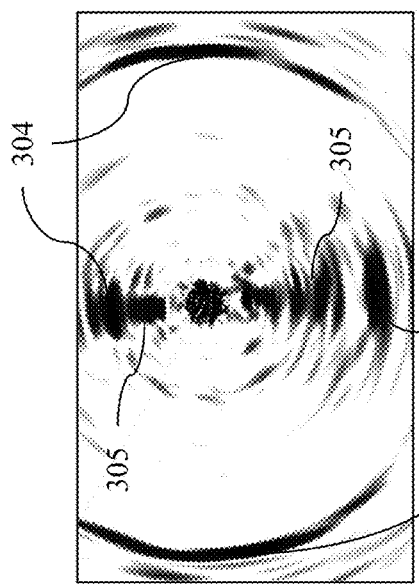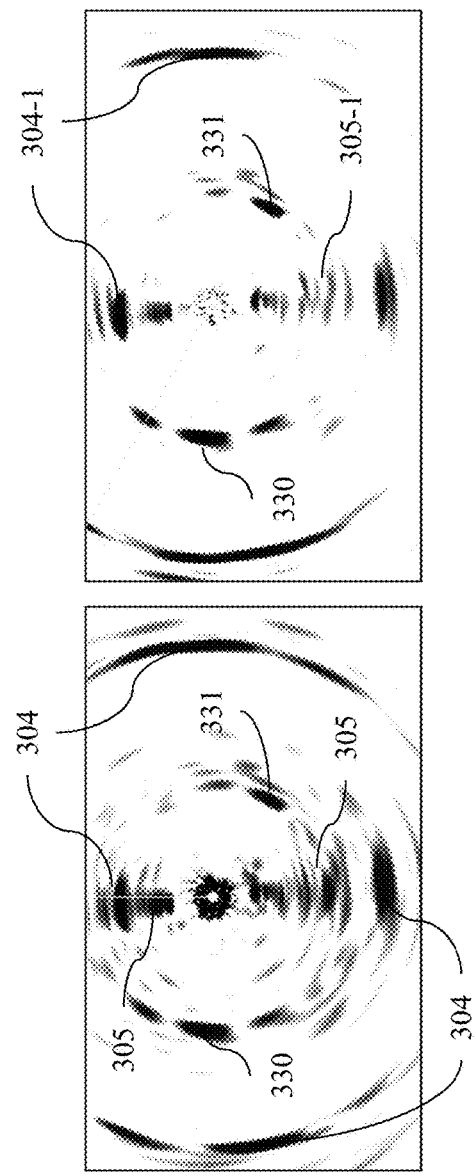
FIG. 22A-2
FIG. 22A-3
FIG. 22A-4

SYSTEMS AND METHODS FOR DAMAGE DETECTION IN STRUCTURES USING GUIDED WAVE PHASED ARRAYS

CROSS-REFERENCE TO RELATED APPLICATIONS

This application is a continuation-in-part of U.S. patent application Ser. No. 13/901,786, filed May 24, 2013, which claims priority to U.S. Provisional Patent Application No. 61/651,864, filed May 25, 2012, the entireties of which are herein incorporated by reference.

FIELD OF DISCLOSURE

The disclosed systems and methods relate to structural heath monitoring and non-destructive examination. More particularly, the disclosed systems and methods relate to structural heath monitoring and non-destructive examination of plates and plate-like structures using guided wave phased arrays.

BACKGROUND

Various systems exist for structural heath monitoring ("SHM") and/or non-destructive examination ("NDE") of plates or plate-like structures like those used on pressure vessels, aircraft fuselage and wings, ship hulls and storage tanks to identify only a couple possible uses. However, these systems and monitoring/examination techniques are mostly based on point-to-point inspections and are not capable of performing rapid large area monitoring and/or inspection.

SUMMARY

In some embodiments, an ultrasonic guided wave system for defect detection in a structure includes at least two guided wave transducers configured to be disposed on a structure and a controller electrically coupled to the at least two guided wave transducers. The controller includes a machine readable storage medium and a processor in signal communication with the machine readable storage medium. The processor is configured to cause a pulse generator to pulse the at least two guided wave transducers in accordance with at least one of time delays or amplitude controls such that guided wave energy is steered in a predetermined direction in the structure or is focused at a predetermined focal point, generate image data of the structure based on the at least one reflected guided wave signal, generate processed image data by performing at least one of baseline image subtraction or image suppression on the image data of the structure, identify a location of at least one possible defect in the structure based on the processed image data, and have defect detection data of the structure including the location of the at least one possible defect in the structure stored in the machine readable storage medium.

In some embodiments, a method for ultrasonic guided wave defect detection in a structure is disclosed. The method includes driving a plurality of transducers to cause guided waves to be transmitted in a structure in a predetermined direction or focused at a predetermined focal point, receiving at least one reflected guided wave signal, and generating image data of the structure based on the at least one reflected guided wave signal. Processed image data are generated by performing at least one of baseline image subtraction or image suppression on the image data of the structure, and a location of the at least one possible defect in the structure is identified and stored in a machine readable storage medium.

In some embodiments, a computer readable storage medium is encoded with program code. When the program code is executed by a processor, the processor performs a method. The method includes causing a plurality of transducers to be driven such that guided waves are transmitted in a structure in a predetermined direction or focused at a predetermined focal point, generating image data of the structure based on at least one reflected guided wave signal, and generating processed image data by performing at least one of baseline image subtraction or image suppression on the image data of the structure. A location of at least one possible defect in the structure is identified based on the processed image data.

BRIEF DESCRIPTION OF THE DRAWINGS

FIG. 1A illustrates one example of a non-destructive inspection system for inspecting plates and plate-like structures in accordance with some embodiments.

FIG. 1B illustrates one example of a portable non-destructive inspection or health monitoring system in accordance with FIG. 1A.

FIG. 1G is one example of a block diagram of a controller of the non-destructive inspection system illustrated in FIGS. 1A and 1B in accordance with some embodiments.

FIG. 2 illustrates one example of phase velocity dispersion curves for a zero degree fiber direction in a 16 layer quasi-isotropic composite plate.

FIG. 3 illustrates one example of an image obtained of a numerical simulation of guided wave energy being steered in a direction in a plate structure.

FIG. 4A illustrates one example of an experimental result of a phased array scanning image obtained by using the wave number domain back-propagation signal synthesis using a 16-element circular array mounted at the approximate center of the plate.

FIG. 4B is a picture of the array used to obtain the image illustrated in FIG. 4A.

FIGS. 4C-4F are detailed images of the defects detected in the image of FIG. 4A.

FIG. 6B illustrates an example of an "exposed" surface on a 4 ft.×4 ft. aluminum plate with two simulated corrosion defects show at the right of the figure.

FIG. 7A illustrates an example of a CT image showing the detection and imaging of Defect 1 in FIG. 6B.

FIG. 7B illustrates an example of a CT image showing the detection and imaging of Defect 2 in FIG. 6B.

FIG. 7C illustrates an example of a CT image showing the detection and imaging of both Defect 1 and Defect 2 in FIG. 6B.

FIGS. 8A and 8B illustrate examples of outside-in focusing using tomography sensors in accordance with some embodiments.

FIG. 10A illustrates one example of a shear sensor in accordance with some embodiments.

FIG. 10B is a high level circuit diagram of a sensor illustrated in FIG. 10A being coupled to an AC power supply in accordance with some embodiments.

FIG. 20A illustrates one example of a diagram from use in calculating time delays for steering guided wave energy into a predetermined direction in accordance with some embodiments.

FIG. 20B illustrates one example of a diagram for use in calculating time delays for focusing guided waves at a predetermined location in accordance with some embodiments.

FIGS. 22A-1-22A-4 illustrate one example of experimental results from phased array SHM imaging in a steel plate using baseline subtraction.

FIGS. 22B-1-22B-3 illustrate one example of experimental results from phased array SHM imaging of a steel plate using baseline subtraction and additional suppression.

FIGS. 22C-1-22C-4 illustrate one example of experimental results from phased array SHM imaging of a steel plate using baseline subtraction and additional stretch suppression.

FIGS. 23A-1 and 23A-2 illustrate the beam directivity profiles with various forms of apodization in accordance with some embodiments.

FIGS. 23B-1 and 23B-2 illustrate a Hamming apodization window in general terms and as applied to a circular phased array.

FIGS. 23C-1 and 23C-2 illustrate one example of experimental results from phased array SHM imaging in a steel plate using apodization to reduce the amplitude of the sidelobes.

DETAILED DESCRIPTION

This description of the exemplary embodiments is intended to be read in connection with the accompanying drawings, which are to be considered part of the entire written description.

Ultrasonic guided waves have shown good potential for SHM and/or NDE of plates or plate-like structures due to their capability of interrogating a large area with a small number of transducer locations. The system and methods disclosed herein utilize a real time phased array concept with specially designed guided wave transducers to produce large area SHM and/or NDE of plates or plate-like structures with improvements on guided wave penetration power, signal-to-noise-ratio (SNR), and defect detection sensitivity. As used herein, the term "plate-like structure" includes plates and refers to a structure confined by two planar or curved surfaces including, but not limited to, those used on pressure vessels, aircraft fuselages and wings, ship hulls, and storage tanks, to list only a few examples.

In some embodiments, the system includes a plurality of ultrasonic guided wave transducers, which can be excited individually and/or simultaneously. In some embodiments, the guided wave transducers are placed closely together on the structure to form a compact array. In some embodiments, the guided wave transducers are distributed on the structure at a distance from each other in a random or orderly configuration. The system includes a number of pulser and receiver channels. Time delays and possible amplitude factors can be input into each pulser channel for steering the guided wave energy in a specific direction or to focus the energy at a specific location in the structure. In some embodiments, guided wave phased array techniques are combined with the guided wave computational tomography ("CT") techniques for damage imaging.

Figure 1D:
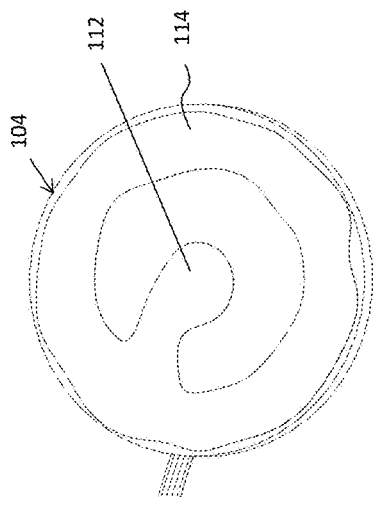
FIG. 1D illustrates one example of the transducers being assembled to the housing illustrated in FIG. 1C in accordance with some embodiments.

FIGS. 1A-1G illustrate one example of a non-destructive inspection system 100 configured to inspect plates and plate-like structures using guided wave phased arrays. As shown in FIG. 1A, inspection system 100 includes a number, n, of transducers 102-1, 102-2, . . . , 102-n (collectively "transducers 102") communicatively coupled to a controller 130. In some embodiments, as described below, system 100 is a portable system in which the transducers 102 are not fixedly connected to a plate or plate-like structure, and in some embodiments, system 100 is a "fixed" system in which the transducers are secured in some manner to a plate or plate-like structure. These transducers 102 can be piezoelectric stack transducers, shear piezoelectric transducers, electrical magnetic acoustic transducers ("EMATs"), or other suitable transducer as will be understood by one of ordinary skill in the art. Transducers 102 can be configured as a transmitter or a receiver in a through-transmission setup. Each of the transducers 102 can also be used as a dual mode transducer under a pulse-echo test mode.

In some embodiments, such as the embodiment in FIG. 1B, a plurality of transducers 102 are arranged in circular phased array 103 disposed in a body or housing 104 of a probe 105 such that the array 103 is portable such that the probe 105 can be placed in contact with plate or plate-like structure 10, be moved around structure 10, and be removed from contact with structure 10. As shown in FIG. 1B, probe 105 is tethered to controller 130. Each of the sensing elements, e.g., transducers 102, can be disposed around body 104 at an equal distance from the directly adjacent sensing elements. In some embodiments, transducers 102 are equally spaced about body 104.

Figure 1F:
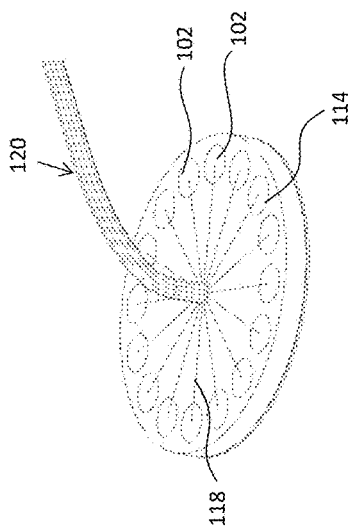
FIG. 1F illustrates one example of the transducers and leads coupled to the transducers being installed in a housing in accordance with some embodiments.
Figure 1C:
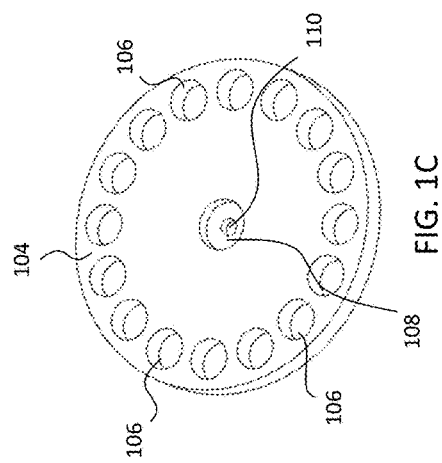
FIG. 1C illustrates one example of a housing for a circular array of transducers in accordance with some embodiments.

FIG. 1C illustrates one example of a housing 104 prior to transducers 102 being installed. As shown in FIG. 1C, housing 104 includes a plurality of holes or internal chambers 106 arranged in a circle near the peripheral edge 108 of housing 104. In some embodiments, housing 104 is formed from Noryl; however, housing 104 can be formed from other materials including, but not limited to, rubber, metal, and plastic to list a few possible alternative materials. Holes and/or internal chambers 106 can be formed by drilling, milling, injection molding housing 104 with holes 106, or by any other suitable manufacturing method. Although a plurality of holes/internal chambers 106 are illustrated, a single hole or internal chamber 106 can be provided and a plurality of transducers can be disposed therein in some embodiments. Housing 104 also defines a slot 108 at the approximate center with a central hole 110 defined within slot 108.

Figure 1E:
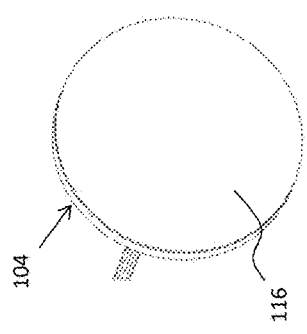
FIG. 1E illustrates one example of a wear plate affixed to the bottom surface of the array housing in accordance with some embodiments.

Bottom surface 112 of housing 104 is covered, at least partially, with a conductive epoxy 114 as shown in FIG. 1D, and then is covered with a wear plate 116 as illustrated in FIG. 1E. In some embodiments, wear plate 116 is formed from a metal material, such as aluminum, although one of ordinary skill in the art will understand that other materials can be used. A ground lead (not shown) may be placed within central hole 110.

Turning now to FIG. 1F, transducers 102 are inserted into holes 106 and sealed therein by epoxy 114. A lead wire 118 is connected to each transducer 102 and, in some embodiments, are tied together in a bundle 120. In some embodiments, the transducers 102 are thin piezoelectric disks, piezoelectric cylinders, cuboid piezoelectric elements, magnetostrictive transducers, such as those disclosed in commonly assigned U.S. patent application Ser. No. 13/298,758, which is incorporated herein by reference in its entirety, EMATs, or other suitable transducer. In some embodiments, the phased array 103 is made from a piece of piezoelectric composite material with an array of electrode patterns. The piezoelectric composite material is enclosed in a housing enclosure with appropriate wiring, transducer backing, matching, and wear plates as will be understood by one of ordinary skill in the art.

Referring now to FIG. 1G, controller 130 includes one or more processors, such as processor(s) 132. Processor(s) 132 may be any central processing unit ("CPU"), microprocessor, micro-controller, or computational device or circuit for executing instructions and be connected to a communication infrastructure 134 (e.g., a communications bus, cross-over bar, or network). Various software embodiments are described in terms of this exemplary controller 130. After reading this description, it will be apparent to one of ordinary skill in the art how to implement the method using other computer systems or architectures.

In some embodiments, controller 130 includes a display interface 136 that forwards graphics, text, and other data from the communication infrastructure 134 (or from a frame buffer not shown) for display on a monitor or display unit 138 that is integrated with or separate from controller 130.

Controller 130 also includes a main memory 140, such as a random access memory ("RAM"), and a secondary memory 142. In some embodiments, secondary memory 142 includes a persistent memory such as, for example, a hard disk drive 144 and/or removable storage drive 146, representing an optical disk drive such as, for example, a DVD drive, a Blu-ray disc drive, or the like. In some embodiments, removable storage drive may be an interface for reading data from and writing data to a removable storage unit 148. Removable storage drive 146 reads from and/or writes to a removable storage unit 148 in a manner that is understood by one of ordinary skill in the art. Removable storage unit 148 represents an optical disc, a removable memory chip (such as an erasable programmable read only memory ("EPROM"), Flash memory, or the like), or a programmable read only memory ("PROM")) and associated socket, which may be read by and written to by removable storage drive 146. As will be understood by one of ordinary skill in the art, the removable storage unit 148 may include a non-transient machine readable storage medium having stored therein computer software and/or data.

Controller 130 may also include one or more communication interface(s) 150, which allows software and data to be transferred between controller 130 and external devices such as, for example, transducers 102 and optionally to a mainframe, a server, or other device. Examples of the one or more communication interface(s) 150 may include, but are not limited to, a modem, a network interface (such as an Ethernet card or wireless card), a communications port, a Personal Computer Memory Card International Association ("PCMCIA") slot and card, one or more Personal Component Interconnect ("PCI") Express slot and cards, or any combination thereof. Software and data transferred via communications interface 150 are in the form of signals, which may be electronic, electromagnetic, optical, or other signals capable of being received by communications interface 150. These signals are provided to communications interface(s) 150 via a communications path or channel. The channel may be implemented using wire or cable, fiber optics, a telephone line, a cellular link, a radio frequency ("RF") link, or other communication channels.

In this document, the terms "computer program medium" and "non-transient machine readable medium" refer to media such as removable storage units 148 or a hard disk installed in hard disk drive 144. These computer program products provide software to controller 130. Computer programs (also referred to as "computer control logic") may be stored in main memory 140 and/or secondary memory 142. Computer programs may also be received via communications interface(s) 150. Such computer programs, when executed by a processor(s) 132, enable the controller 130 to perform the features of the method discussed herein.

In an embodiment where the method is implemented using software, the software may be stored in a computer program product and loaded into controller 130 using removable storage drive 146, hard drive 144, or communications interface(s) 150. The software, when executed by a processor(s) 132, causes the processor(s) 132 to perform the functions of the method described herein. In another embodiment, the method is implemented primarily in hardware using, for example, hardware components such as application specific integrated circuits ("ASICs"). Implementation of the hardware state machine so as to perform the functions described herein will be understood by persons skilled in the art. In yet another embodiment, the method is implemented using a combination of both hardware and software.

Controller 130 also includes a pulse generator 152 configured to output a variety of pulses to transducers 102. For example, pulse generator 152 may transmit time-delayed control signals to transducers 102, and/or pulse generator 152 may transmit control signals of varying amplitudes to transducers 102.

An amplifier 154 is configured to amplify signals received from transducers 102. Such signals received by transducers 102 include reflections of waves from structural features and other anomalies, e.g., corrosion in a plate or plate-like structures, in response to signals transmitted by pulse generator 152. An analog to digital ("A/D") converter 156 is coupled to an output of amplifier 154 and is configured to convert analog signals received from amplifier 154 to digital signals. The digital signals output from A/D converter 156 may be transmitted along communication infrastructure 134 where they may undergo further signal processing by processor(s) 132 as will be understood by one of ordinary skill in the art.

Figures 1, 22A:
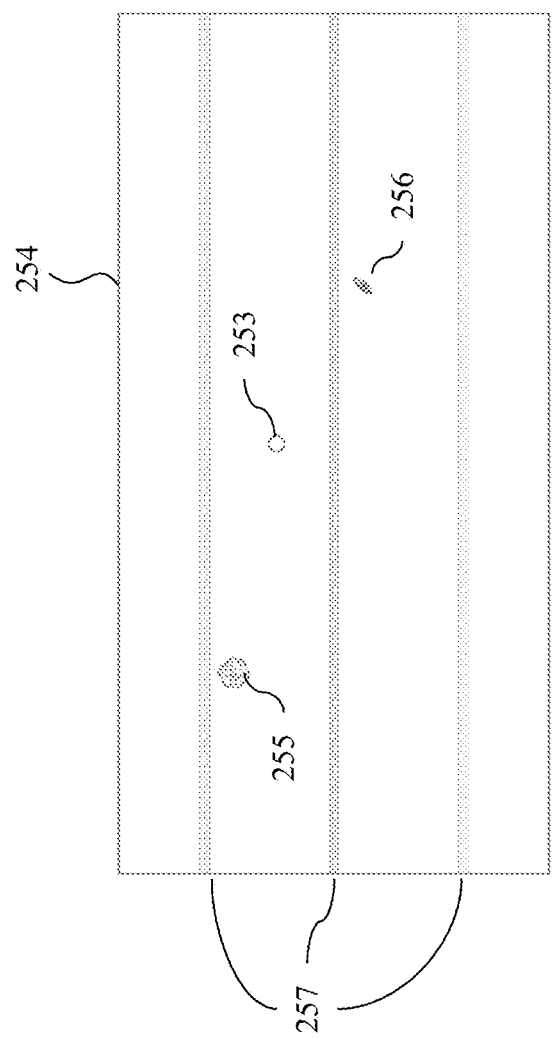
Figures 1, 22B:
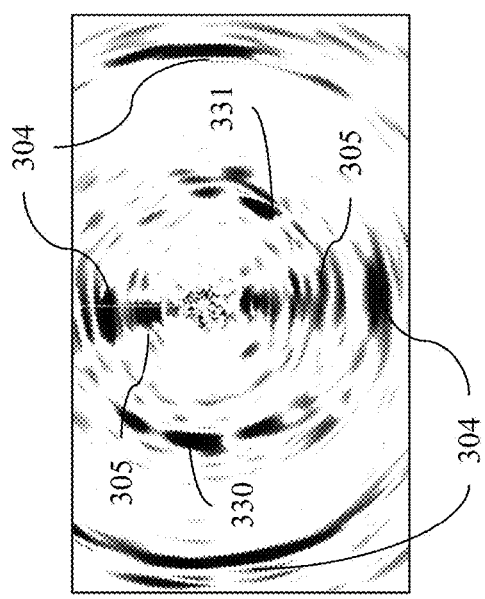
Figures 3, 22B:
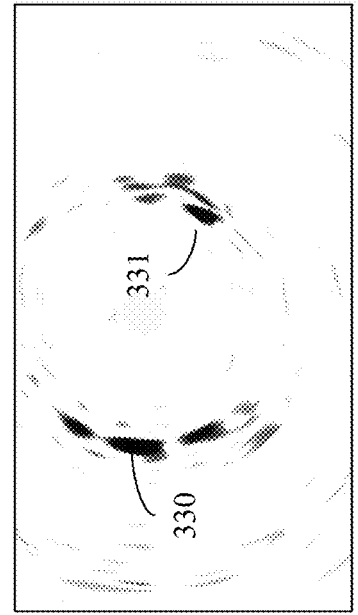
Figures 2, 22B:
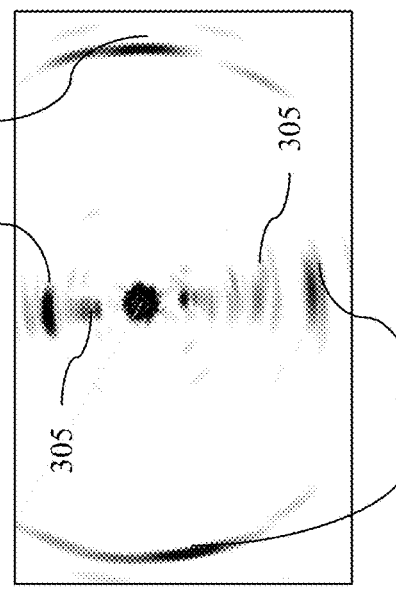

Turning now to FIG. 2, which illustrates one example of velocity dispersion curves for a zero degree fiber direction in a 16 layer quasi-isotropic composite plate with the first 8 modes by their respective numbers, i.e., 1, 2, 3, etc. There are infinite numbers of possible guided wave modes in a plate-like structure such as, for example, a composite plate. These wave modes in a plate have different phase and group velocities and energy distributions across the thickness, which may vary with frequency and/or excitation conditions. For guided wave beam steering or beam focusing, guided wave modes with similar velocities can be excited.

The guided wave modes with different velocities are considered as unwanted wave modes and may result in significant wave energy traveling to directions other than the desired beam steering direction or create energy focal points other than at the desired focal point. Furthermore, the velocity differences may introduce coherent noise in guided wave damage detection applications. For instance, if the pulse-echo method is used to detect a single defect, the received signal may have multiple reflected wave packets due to the existence of wave modes with different wave velocities. The redundant wave packets coming from the unwanted wave modes may cause false alarms. To avoid the influence of the unwanted wave modes, transducers with the capability of dominantly exciting guided wave energy with the desired wave velocity while minimizing the energy of the unwanted wave modes can be used. The design of such transducers can be carried out based on theoretical calculations. As described above, examples of such guided wave transducers include, but are not limited to, annular array transducers, time delay annular array transducers, piezoelectric elements on angle wedges, EMATs, and magnetostrictive transducers, to list a few possibilities.

With the energy of unwanted wave modes controlled, time delays can be applied to the transducers 102 to perform phased array beam steering or focusing. Each transducer 102 in the array 103 excites guided wave energy that can propagate in any direction. As described above, pulse generator 152 can transmit time-delayed control signals to transducers 102 to physically focus guided waves at a focal point or to form a guided wave beam in a particular direction. The direction of wave propagation can be controlled via a "phasing" approach. FIG. 3 illustrates one example of the image obtained using a circular phased array of a portable system 100, such as an array 103 of probe 105 described above in accordance with FIGS. 1B-1F, inspecting an aluminum plate. As shown in FIG. 3, by applying time delays to the array 103, the individual transducer elements 102 can be "phased" in such a way to allow the guided wave energy to be steered in any direction.

The steering direction can then be controlled to allow 360° scanning. This is different from the guided wave array systems for plate structures that are presented in the articles "Tuned Lamb Wave Excitation and Detection with Piezoelectric Wafer Active Sensors for Structural Health Monitoring," by V. Giurgiutiu; "Directional Piezoelectric Phased Array Filters for Detecting Damage in Isotropic Plates," by Purekar et al.; "Omni-Directional Guided Wave Transducer Arrays for the Rapid Inspection of Large Areas of Plate Structures," by P. D. Wilcox; and "On the Development and Testing of a Guided Ultrasonic Wave Array for Structure Integrity Monitoring," by Fromme et al., the entireties of which are incorporated by reference herein. In those systems, only one element of an array is pulsed at a time, and, as a result, there are no physically formed guided wave beams. The "beam steering" or "focusing" of those arrays are conducted through post data acquisition signal processing only.

In contrast, the systems and methods disclosed herein generate a physically formed beam of guided wave energy and direct such physically formed beam to different directions by varying the phase delays applied to the different elements of the phased array in a so-called "real-time phased array approach." Benefits of using the real-time phased array approach for guided wave inspection of plate structures include, but are not limited to, higher penetration power, better signal-to-noise ratio, and the capability of rapidly scan selected directions and/or locations, to list a few examples.

In some embodiments, hardware time delays are applied to a probe to physically form guided wave beams for different beam steering directions, and a back propagation wave number domain signal synthesis approach is utilized for the syntheses of both the pulse-echo signals received by the elements 102 of the phased array and the through-transmission signals received by the receiving array 103. The back propagation wave number domain signal synthesis approach can be used in favor of a delay-and-sum time domain approach. Using plate structures as an example and taking into account the guided wave dispersion and the wave divergence in the plate, the time signal at a point located in the far field of an array element can be approximately expressed as:

$$s'(t) = \frac{1}{\sqrt{x}} \int_{-\infty}^{\infty} S(\omega) e^{-ik(\omega)x} d\omega \qquad \text{Eq. (1)}$$

Where, $S(\omega)$ is the Fourier transform of the time domain guided wave input signal;

x is the distance away from the array element; and k represents the wave number.

The wave number k is a function of circular frequency ω for guided wave modes with dispersion. For the pulse-echo mode, the reflected guided wave signal introduced by a defect located in the far field of the array can then be approximately written as:

$$G_n(t) = \frac{\gamma\delta}{r_d} \int_{-\infty}^{\infty} S(\omega) e^{-ik(\omega)2r_d} e^{ik(\omega)d_n} d\omega \qquad \text{Eq. (2)}$$

Where, where δ is the signal magnification coefficient introduced by the constructive interference of the signals generated by all of the phased elements;

γ is the reflection coefficient;

$r_d$ is the distance from the defect to the center of the array;

the subscript n represents that the reflection is received by the nth array element; and d denotes the propagation distance that needs to be compensated for beam steering to the angle where the defect locates.

The wave number domain signal synthesis of the signals described by Equation (2) can be conducted using the following equation:

$$\sum_n B_n G_n(t) = \frac{\gamma\delta N}{r_d} \int_{-\infty}^{\infty} S(\omega) e^{-ik(\omega)2r_d} d\omega \qquad \text{Eq. (3)}$$

Where,

N is the number of array elements, and $B_n$ is the back-propagation term:

$$B_n = e^{-ik(\omega)d_n} \qquad \text{Eq. (4)}$$

As shown in Equation (4), the dispersion relation of the guided wave modes is included in the back-propagation process so that the dispersion effects that could decrease defect detection resolution can be removed from the wave number domain synthesized signals. In some embodiments, Equation (3) can be implemented using Fast Fourier Transforms ("FFT"). The wave number domain signal synthesis is therefore also fast. An advanced deconvolution method can be combined with the real-time guided wave phased array and the wave number domain signal synthesis as well to suppress image artifacts caused by the side lobes of the phased array as disclosed in the Ph.D. thesis, "Ultrasonic Guided Wave Phased Array for Isotropic and Anisotropic Plates," by F. Yan, the entirety of which is herein incorporated by reference.

FIG. 4A illustrates one example of a phased array scanning image obtained in an experiment on a 4 ft.×4 ft. aluminum plate (1 mm thick) using the wave number domain signal synthesis with a fixed system 100 where the transducers 102 were secured to the plate 10. A 16-element circular array 103 was mounted or otherwise secured to the approximate center of the plate using epoxy 114 as illustrated in FIG. 4B. Lead wires 118 electrically connected array 103 to a controller 130 (not shown). The phased array was operated under a pulse-echo mode, and the locations and shapes of the defects are indicated in the image for comparison. As can be seen, defects 12, 14 16, and 18, which are shown in FIGS. 4C, 4D, 4E, and 4F, respectively, were well detected and located. A 5 mm hole 20 was also detected and is visible in the image.

In some embodiments, computed tomography ("CT") imaging techniques, such as those disclosed in "Ultrasonic Guided Wave Tomography in Structural Health Monitoring of an Aging Aircraft Wing," by Gao et al., and "Large Area Corrosion Detection in Complex Aircraft Components using Lamb Wave Tomography," by Royer et al., the entireties of which are herein incorporated by reference, are used in combination with guided wave activation and reception to accurately detect and locate corrosion and cracking in plate and pipe structures using a small number of sensors to interrogate relatively large areas. Using such a technique, a set of base-line data is acquired and then compared to subsequent data sets, and a CT image is generated by comparing changes in the guided wave signals that occur from damage being introduced into the part.

Figure 5B:
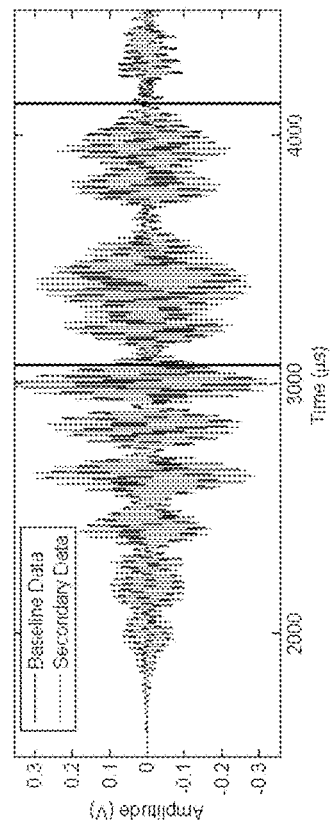
FIG. 5B illustrates one example of guided wave signals between a first transducer pair in FIG. 5A before a corrosion and after a corrosion.
Figure 5C:
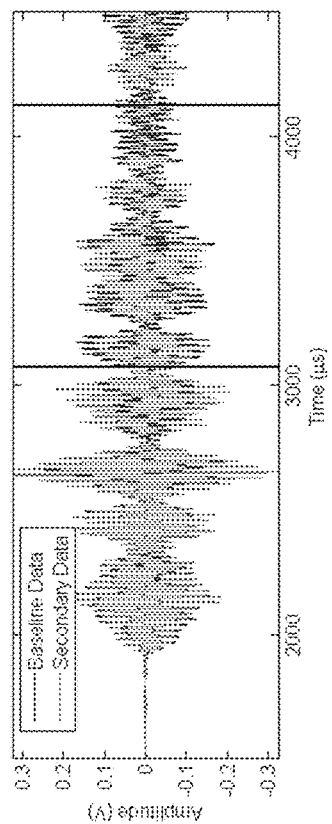
FIG. 5C illustrates one example of guided wave signals between a second transducer pair in FIG. 5A before a corrosion and after a corrosion.
Figure 5A:
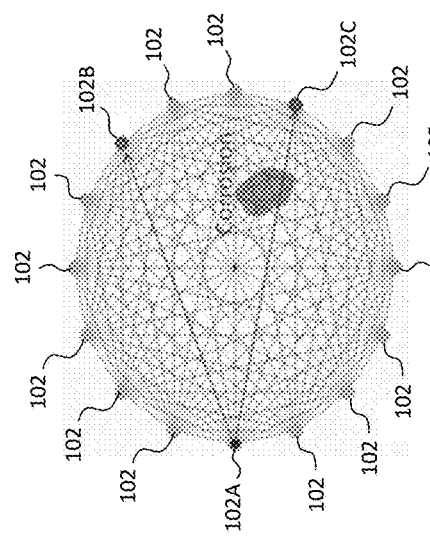
FIG. 5A illustrates one example of a guided wave CT, including the possible paths for a 16-element circular array network.

FIGS. 5A-5C illustrate one example of the guided wave CT concept. All possible guided wave paths for a 16-element guided wave actuator/sensor network are illustrated in FIG. 5A. The guided wave actuators/sensors can be piezoelectric disk transducers, annular array transducers, magnetostrictive transducers, EMATs, or other suitable actuator/sensor. For structural health monitoring ("SHM") applications, base-line guided wave signals are collected for all wave paths. Subsequent data sets are acquired in the same manner over time. Guided wave signal variations can be observed when damage occurs in the area covered by the wave paths. Apparently, the signal variations for different sensor pairs will be different. For example, the sensor pair 102A-102B in FIG. 5A produces consistent signals before and after the corrosion damage occurs as illustrated in FIG. 5B. That is simply due to the fact that the corrosion damage is away from the wave path. In contrast, the sensor pair 102A-102C in FIG. 5A produces significant signal variations before and after the corrosion because the damage is located in the wave path as illustrated in FIG. 5C. The systems disclosed herein include guided wave CT algorithms that utilize the signal variations for different wave paths to reconstruct CT images that reveal the location, approximate size, and severity of possible damage to the structure under monitoring. The algorithms are applicable to sensor arrays with arbitrary sensor placements and also take into account guided wave beam divergence in plate-like structures. Examples of such algorithms are disclosed in "Ultrasonic Guided Wave Tomography in Structural Health Monitoring of an Aging Aircraft Wing," by Gao et al., and "Large Area Corrosion Detection in Complex Aircraft Components using Lamb Wave Tomography," by Royer et al., the entireties of which are herein incorporated by reference.

Different features of the guided wave signal, such as amplitude ratios of different modes and/or time of flight, can be input into the reconstruction algorithm, which is executed by processor(s) 132 of controller 130. Other features could come from a Fourier Transform, a short time Fourier Transform spectrogram, or a wavelet transform as examples. Different features are sensitive to different types of damage or material conditions.

Figure 6A:
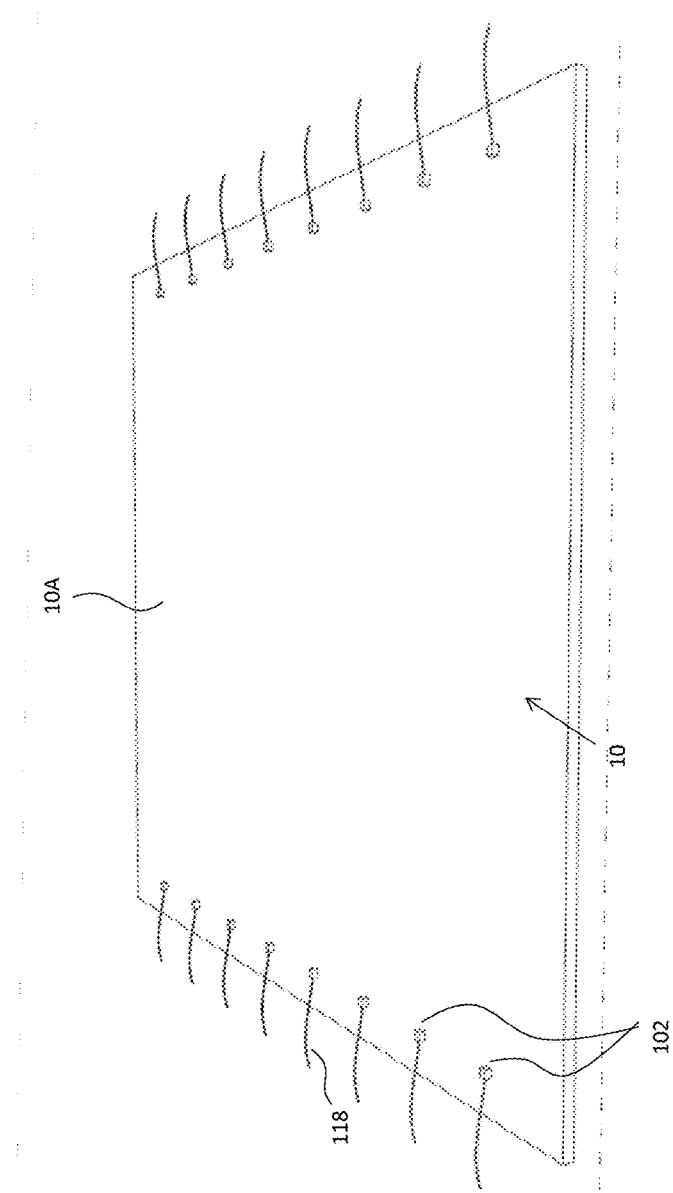
FIG. 6A illustrates an example of a "hidden" surface on a 4 ft.×4 ft. aluminum plate with a 16-sensor linear array mounted on the plate.

FIG. 6A illustrates one example of a first side 10A of a 4 ft. by 4 ft. aluminum plate 10 on which 16 packaged piezoceramic sensors 102 are fixedly mounted (using epoxy or other adhesive) and electrically connected to a controller 130 (not shown) via leads 118. FIG. 6B illustrates the opposite side 10B of the aluminum plate 20, which includes first and second defects, i.e., Defect 1 and Defect 2, respectively. FIGS. 7A-7C illustrate sample results of data that were acquired before and after introducing the simulated corrosion defects on the "exposed" surface FIG. 6B, i.e., before and after Defect 1 and Defect 2 were formed. In particular, FIG. 7A illustrates an example of a CT image showing the detection and imaging of Defect 1 in FIG. 6, FIG. 7B illustrates an example of a CT image showing the detection and imaging of Defect 2 in FIG. 6, and FIG. 7C illustrates an example of a CT image showing the detection and imaging of both Defect 1 and Defect 2 in FIG. 6.

In some embodiments, piezoelectric disc transducers 102, and/or guided wave transducers 102 with guided wave mode and frequency selection capabilities are used as guided wave CT sensors. Examples of guided wave sensors 102 include, but are not limited to, annular array transducers, time delay annular array transducers, piezoelectric elements on angle wedges, EMATs, and magnetostrictive transducers, to list just a few possibilities.

Ultrasonic guided wave signals taken from a guided wave CT system are generally complicated, and this is especially true when using guided wave CT for large area monitoring of structures with complex geometries, for instance, rivets, and stiffeners. The multiple guided wave scatterings and possible mode conversions at the geometry variations make guided wave signals hard to integrate. This is the main reason why most current guided wave CT systems use only the so-called damage indexes ("DI") that are defined based on some overall changes in guided wave signals. An example of such a system is described in "Detection and Monitoring of Hidden Fatigue Crack Growth Using a Built-in Piezoelectric Sensor/Actuator Network: II. Validation Using Riveted Joints and Repair Patches," by Ihn et al., the entirety of which is herein incorporated by reference.

With the controlled guided wave excitations provided by the guided wave transducers, the quality of the guided wave signals can be greatly increased, in the sense that the signals become much easier to integrate based on the knowledge of the guided wave inputs. Physically based guided wave features may then be extracted from the guided wave signals for damage detection and evaluation. Examples of such physically based features include, but are not limited to, amplitude ratios of different modes, mode conversions among different guided wave modes, phase shifts of a specific mode, TOF changes of different modes, and changes in dispersion characteristics, to list a few non-limiting examples.

Guided wave signals obtained with these types of transducers are easier to interpret due to the controlled guided wave input. However, because of possible wave scatterings and mode conversions which are actually quite common for structures with complex geometries such as rivets and stiffeners, advanced signal processing methods are used for accurate feature extractions. Many signal processing tools are available for guided wave signal analysis including, but not limited to, FFT based spectrogram, wavelet based scalogram, and Hilbert-Huang transform. Each of these signal processing techniques can be used to obtain time-frequency representations of guided wave signals for in-depth guided wave mode and frequency analyses.

Figure 9:
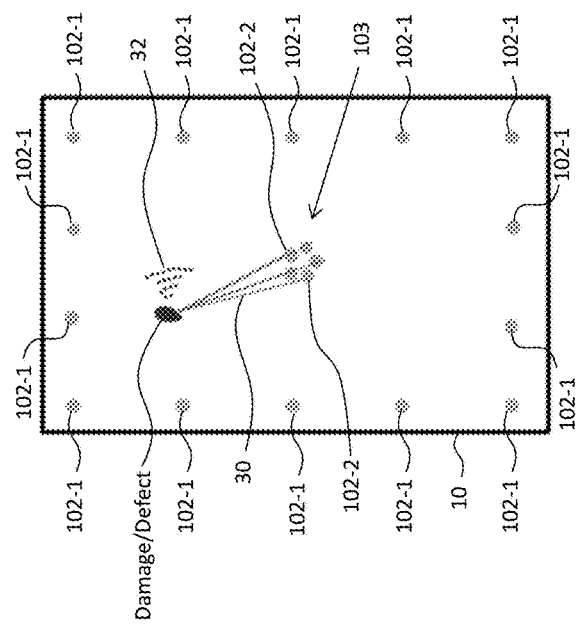
FIG. 9 illustrates one example of using tomography sensors to improve the performance of a phased array.

In some embodiments, the two technologies, guided wave phased array beam steering and guided wave tomography, can be combined together to provide more reliable damage detection and characterization as well as to potentially reduce the sensor density. FIGS. 8A, 8B, and 9 illustrate examples of the combination of the two technologies. Referring first to FIG. 8A, a plate-like structure 00 is provided with a plurality of sensors 102 being positioned about the periphery of plate 10.

As shown in FIGS. 8A and 8B, a number of sensors 102 are placed close to the boundary of the plate-like structure 10 for guided wave tomography tests. In some embodiments, tomography sensors 102 are thin piezoelectric disks, piezoelectric cylinders, cuboid piezoelectric elements, magnetostrictive transducers, and EMATs, to list a few possibilities. Using the phased array concept, different phase delays can be applied to the tomography sensors 102 by pulse generator 152 of controller 130 (not shown) to generate physical guided waves in a particular direction to focus from outside-in or from random locations, i.e., to achieve constructive interferences at different locations. The constructive interferences can increase the guided wave energy for damage interrogation and therefore will yield better penetration distance and more reliable damage detection results.

Phase delays may also be applied two or more of the tomography sensors 102 to focus guided wave energy to or close to the locations of other tomography sensors 102. Higher penetration power can be achieved with the phased array focusing. The phased delays may be applied to any tomography sensor groups. The locations of the focal points may be switched among different sensor locations as well. The received signals can be used for tomographic image reconstructions. In SHM applications, the "phasing" process can also be done with the residual signals that are calculated by subtracting base-line signals from the subsequently acquired signals. These calculations can be performed by processor(s) 132 of controller 130 as will be understood by one of ordinary skill in the art.

In FIG. 9, a plate or plate-like structure 10 is monitored using both tomography sensors 102-1 placed close to the plate edges and a probe 105 (not shown) including a phased array 103 of transducers 102-2 located near the center of the plate 10. Transducers 102-2 of array 103 is used to direct guided wave energy 30 in different directions by steering the energy as described above. At least some of the guided wave energy is reflected or scattered by a Damage/Defect in plate 10. This reflected/scattered guided wave energy, which is referenced by reference numeral 32, can be detected by tomography sensors 102-1. Thus, the combination of tomography sensors 102-1 and array 103 increase the probability of detection of scattered guided wave energy 32, which is reflected/scattered at different angles. All scattered guided waves can be well recorded. Again, a phasing process may be applied to the signals received by the tomography sensors 102-1 to further improve the inspection results.

System 100 can also be used to inspect plate and plate-like structures that are subject to water loading conditions, such as ship hulls, storage tank floors, and the like. In such embodiments, guided wave transducers 102 are designed such that they will excite and/or receive guided wave energies that do not leak into water. Shear horizontal ("SH") type guided waves with pure shear particle displacements on the structure surfaces do not leak into water and therefore are one example of a suitable transducer 102 for this type of application. Longitudinal type waves with dominant in plane displacement on the surface of a structure may also be used.

Referring now to FIGS. 10A and 10B, one example of a sensor 102A in accordance with some embodiments. Sensor 102 illustrated in FIG. 10A is implemented as a shear transducer and is based on a small shear polarized $d_{15}$ PZT element. The transducers/sensors 102A are designed for the excitation and reception of SH type waves. As best seen in FIG. 10A, transducer 102A includes a piezoceramic block 158 sized and configured to be received within an internal chamber defined by housing 160. Conductive leads 162, such as coaxial cable or other electrical wiring, are coupled to housing 160 and are disposed within a conduit 164 for electrical connection to a controller 130 (not shown). As can be seen in FIG. 10A, the size of sensor 102A is less than that of a dime. In some embodiments, piezoceramic block 158 is glued or fixed in housing 160 using a conductive epoxy, glue, or soldering. The internal chamber of housing 160 can be back filled with epoxy or soldering to improve the robustness of sensor 102A. An AC voltage 166 is applied to piezoceramic block 158 by conductive leads 162 as illustrated by the circuit diagram in FIG. 10B to provide shear deformations of the piezoceramic block 158.

Shear sensors 102A in accordance with FIGS. 10A and 10B were designed and tested using a fixed system 100 where the sensors 102A were fixedly coupled to plate or plate-like structure 10. These tests demonstrate that shear sensors 102A reduce and/or eliminate any negative effects, such as false alarms caused by water loading conditions, when performing guided wave SHM/NDE (nondestructive evaluation).

Figure 11B:
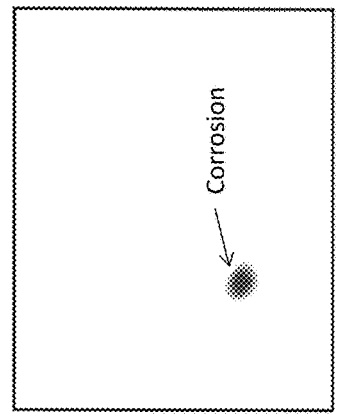
FIG. 11B illustrates one example of a corrosion detection result obtained using a shear sensor setup under the water loading condition in accordance with FIG. 11A.
Figure 11D:
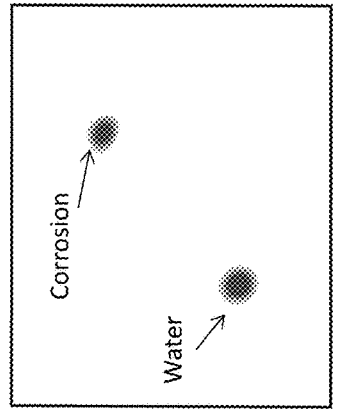
FIG. 11D illustrates one example of a corrosion detection result obtained using a PZT disk sensor setup in accordance with FIG. 11C.
Figure 11A:
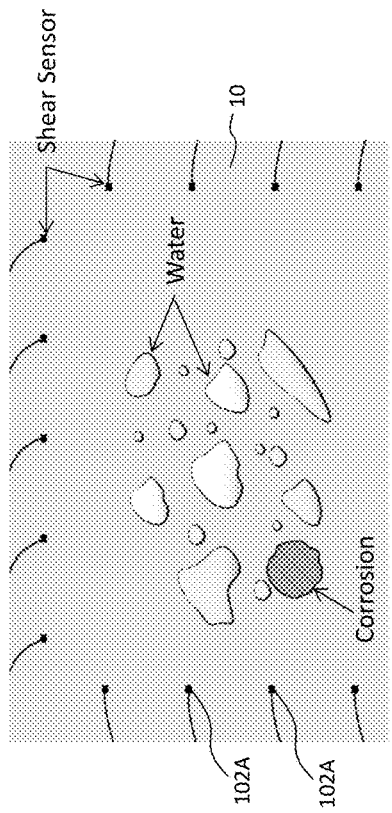
FIG. 11A illustrates one example of a shear sensor setup for corrosion detection under a water loading condition.

For example, FIG. 11A illustrates one example of a plurality of shear sensors 102A disposed on a surface of a plate 10 having a defect or damage in the form of corrosion thereon. FIG. 11B shows the results of performing SHM/NDE of the setup illustrated in FIG. 11B. As shown in FIG. 11B, a system 100 configured with shear sensors 102A was able to sense the corrosion on plate 10 as the corrosion is visibly presented in FIG. 11B.

Figure 11C:
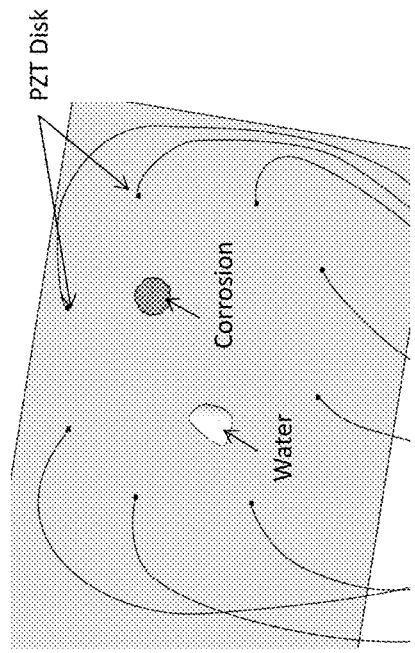
FIG. 11C illustrates one example of a PZT disk sensor setup under a water loading condition.

FIGS. 11A and 11B are in contrast with FIGS. 11C and 11D, which illustrate a piezoelectric sensor setup under a water loading condition where the piezoelectric sensors were not $d_{15}$ PZT elements and the resultant image, respectively. As shown in FIG. 11D the water present on plate 10 in FIG. 11C triggered a false detection of corrosion that was not present in FIG. 11B.

Figure 12:
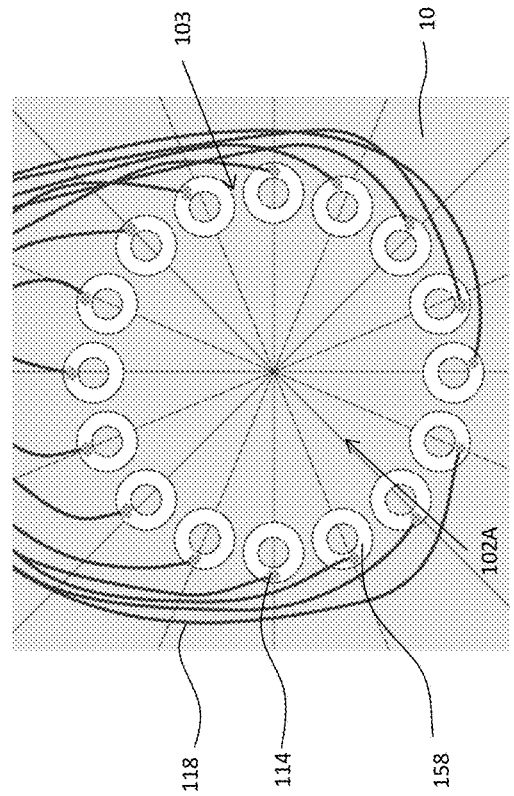
FIG. 12 illustrates one example of a circular shear PZT element array including 16 elements in accordance with some embodiments.
Figure 13D:
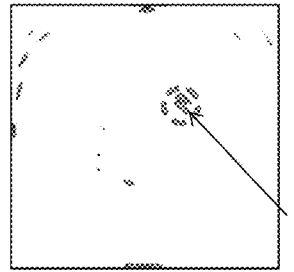
FIG. 13D illustrates one example of the results obtained for a corrosion defect at its stage 1 with water as detected by the array illustrated in FIG. 12.
Figure 13C:
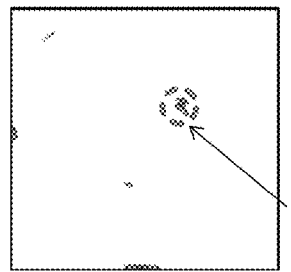
FIG. 13C illustrates one example of the results obtained for a corrosion defect at its stage 3 with no water as detected by the array illustrated in FIG. 12.
Figure 13B:
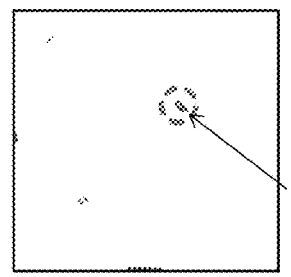
FIG. 13B illustrates one example of the results obtained for a corrosion defect at its stage 2 with no water as detected by the array illustrated in FIG. 12.
Figure 13A:
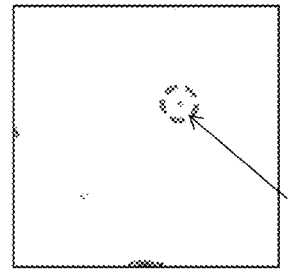
FIG. 13A illustrates one example of the results obtained for a corrosion defect at its stage 1 with no water as detected by the array illustrated in FIG. 12.

The shear polarized d15 PZT elements 102A can also be used to form a compact phased array for guided wave beam steering. For example, FIG. 12 illustrates an example shear PZT element array 103 disposed in a circular arrangement that is fixedly attached to a plate or plate-like structure 10. Each element 102A of the array 103 included a piezoceramic block 158 was mounted to the surface of a 0.375" thick aluminum plate 10 that simulates a section of a ship hull. The results of the phased array defect detection of the setup illustrated in FIG. 12 for monitoring the growth of a corrosion defect are shown in FIGS. 13A-13D. The corrosion defect was simulated by pitting. The density of the pit holes was increased to simulate defect growth. Three defect growth stages were monitored. FIGS. 13A-13D present the phased array images for stages 1, 2, and 3 of the growth of the corrosion defect, respectively. The phased array data for FIGS. 13A-13C were collected when the plate was dry. FIG. 13D shows the phased array image for the corrosion defect at stage 3 with the plate 10 subject to water loading. Clear defect indications can be seen in all four figures. The locations of the defect indications also very well agree with the actual corrosion defect location.

As described above, the system 100 can be configured to be portable with a probe 105 including an array 103 of guided wave phased array sensors 102 as illustrated in FIG. 1B. In some embodiments, sensors 102 are formed from $d_{33}$ PZT elements, $d_{15}$ shear PZT elements, magnetostrictive transducer elements, or EMAT elements, to list just a few possibilities. Such a portable system 100 can be used for NDE of ship hulls or other structures comprising plates or plate-like structures.

Figure 14B:
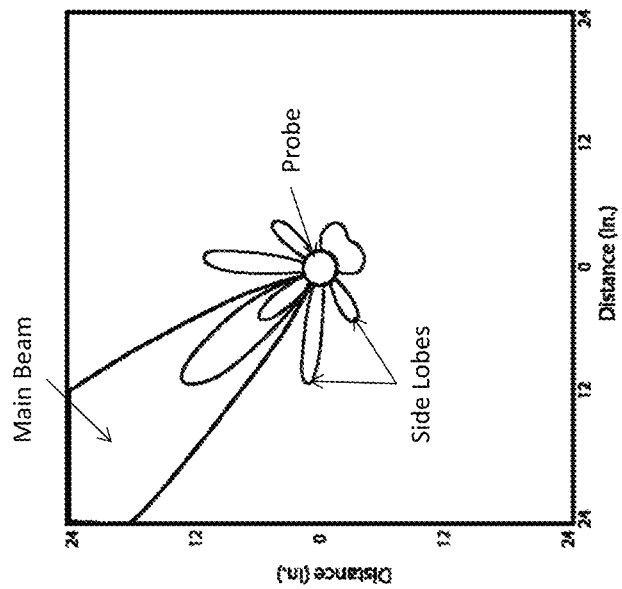
FIGS. 14A and 14B illustrate scanning images of a representation of a ship hull structure using a pulse-echo phase array probe in accordance with FIG. 1B.
Figure 14A:
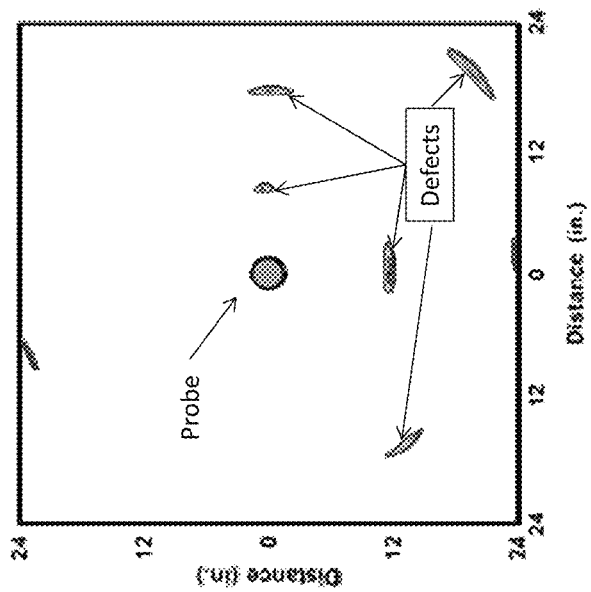

FIGS. 14A and 14B illustrate a pulse-echo phased array scanning image of a representation of a ship's hull. As shown in FIG. 14A, guided wave beam steering sends guided waves into different directions to look for defects, and FIG. 14B illustrates the defects identified by the probe. In pulse-echo mode, the transducers 102 of the phased array probe 105 detects defect reflections that propagate back to the probe position. The defect locations are determined by the beam steering angle, the time-of-flight ("TOF") of the defect reflections, and the guided wave velocity. A pulse-echo phased array scanning image of the structure being inspected can be generated by varying phased array time delays to scan the regions of interest as shown in FIG. 14B. Such an image can be presented to a user on display 138 of controller 130.

Figure 15B:
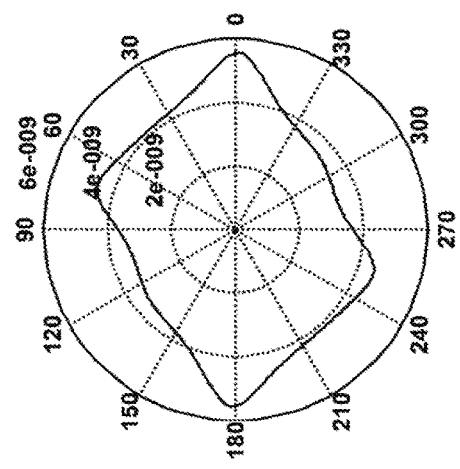
FIG. 15B illustrates one example of angular dependence of out-of-plane displacement of mode 1 at a frequency of 160 kHz excited by a unit out-of-plane point source.
Figure 15A:
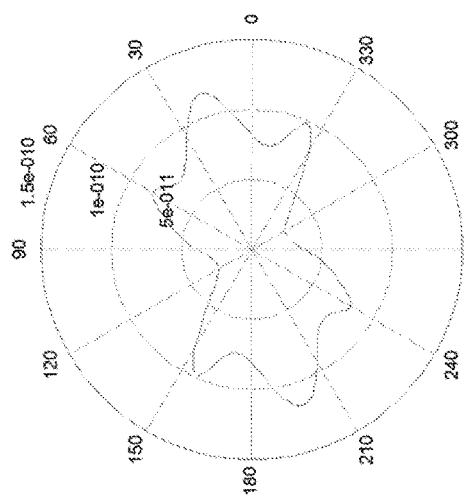
FIG. 15A illustrates one example of angular dependence of out-of-plane displacement of mode 3 at a frequency of 600 kHz excited by a unit out-of-plane point source.

System 100 can be used for anisotropic multilayer composite plates or plate-like structures. As guided wave excitations become more complex when material anisotropy is involved, a Green's function based theoretical method can be employed to study the guided wave excitations in composite plate like structures as described in "Ultrasonic Guided Wave Phased Array for Isotropic and Anisotropic Plates," by Yan. Amplitude and phase variations of the guided wave field excited by a point source applied normally to a composite plate are non-axisymmetric, but the point source itself can be considered as an axisymmetric loading. The angular dependencies of the amplitude for the mode 3 at 600 kHz and the mode 1 at 160 kHz calculated using the Green's function based method are shown in FIGS. 15A and 15B, respectively. As can be seen by comparing FIGS. 15A and 15B, the amplitude of the mode 3 changes much more dramatically as compared to the one of mode 1. The phased array beam steering directivity profile of a circular array for a composite plate can be calculated as:

$$p(\phi) = \sum_n \alpha_g(\phi)\exp\{-iR[\Phi_g(\phi)\cos(\psi_n - \phi) - \Phi_g(\phi_0)\cos(\psi_n - \phi_0)]\} \qquad \text{Eq. (5)}$$

Where, where $\alpha_g(\phi)$ represents the angular dependence of the guided wave amplitude;

$\Phi_g(\phi)$ is the corresponding angular dependence of phase variations,

R denotes the radius of the array,
$\psi_n$ denotes the angular locations of the array elements, and
$\phi_0$ is the beam steering angle.

Figure 16B:
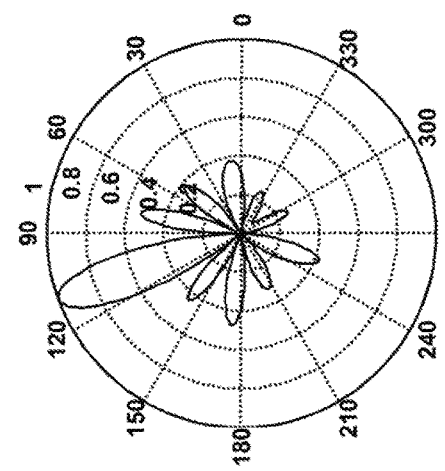
FIG. 16B illustrates one example of phased array beam steering of mode 1 at 160 kHz at a 110 degree beam steering direction.
Figure 16A:
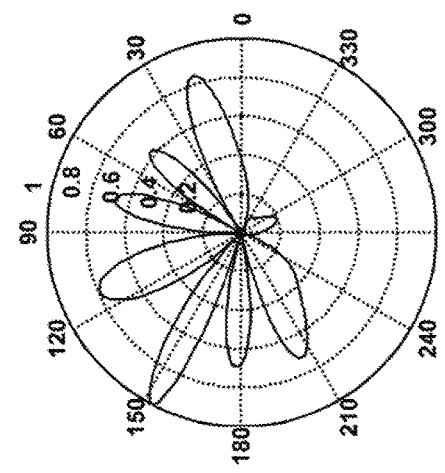
FIG. 16A illustrates one example of phased array beam steering of mode 3 at 600 kHz at a 113 degree beam steering direction.

Sample directivity profiles for the mode 3 at 600 kHz and the mode 1 at 160 kHz are given in FIGS. 16A and 16B, respectively. From FIG. 16A, it can be seen that although the beam steering direction is 113 degrees, the strongest beam of the phased array output is close to the 150 degree direction, and the beam steering fails in other directions. The beam steering failure is due to the amplitude of the mode 3 reaching its minimum at the 113 degree direction as shown in FIG. 15A. The large amplitudes of the excited wave in other directions form strong side lobes.

In contrast, the mode 1 beam steering directivity profile for the 110 degree direction, which is the minimum amplitude direction for the mode 1, demonstrates a good beam steering capability in FIG. 16B. This is due to the fact that the amplitude variations of the mode 1 are much less severe than the mode 3. Thus, choosing the wave mode with less amplitude changes in different directions ensures good guided wave beam steering for all directions. Such selection can be made by reviewing the directivity profiles when developing signal processing and defect imaging algorithms.

Figure 17:
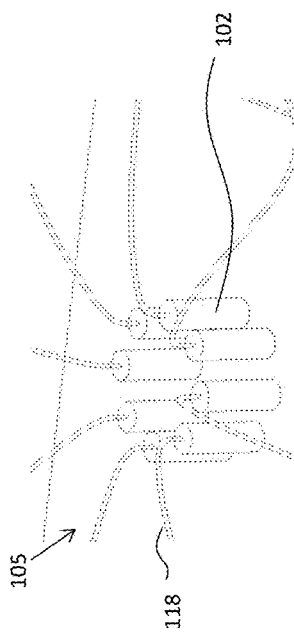
FIG. 17 illustrates one example of an 8-element sensor array including a rod sensing element for exciting mode 1 in a composite plate at 100 kHz.

An example guided wave phased array probe 105, which includes a plurality of transducers 102 that are electrically coupled to a controller 130 (not shown), designed for beam steering in a composite plate is shown in FIG. 17. The composite array was designed for good beam steering directivity profiles for all directions in a 0.24 inch thick carbon composite plate. The mode 1 at 100 kHz was selected for such applications because the mode 1 is not sensitive to fiber orientations at low frequencies. As a result, the amplitudes of the mode 1 for different directions are close to each other.

Figure 18C:
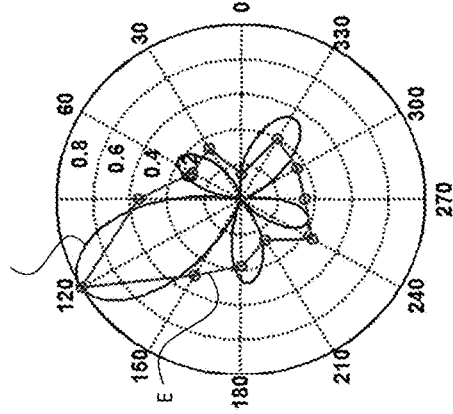
FIG. 18C illustrates a comparison between experimental results and a calculated array defectivity profile for a beam steering angle of 120 degrees.
Figure 18B:
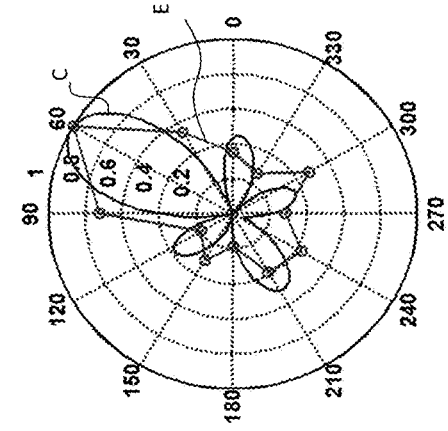
FIG. 18B illustrates a comparison between experimental results and a calculated array defectivity profile for a beam steering angle of 60 degrees.
Figure 18A:
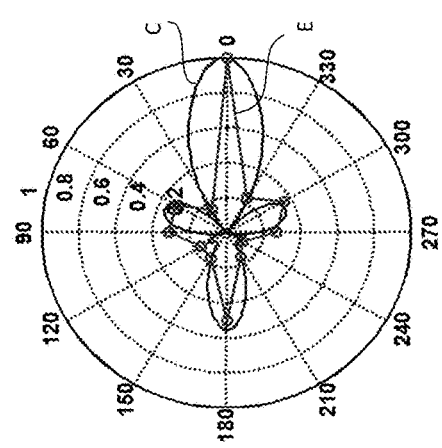
FIG. 18A illustrates a comparison between experimental results and a calculated array defectivity profile for a beam steering angle of zero degrees.

FIGS. 18A-18C illustrate comparisons between the measured directivity profiles of the array 103 and the theoretically calculated profiles. For example, FIG. 18A illustrates a comparison between experimental results (trace "E") and a calculated array defectivity profile (trace "C") for a beam steering angle of zero degrees. FIG. 18B illustrates a comparison between experimental results (trace "E") and a calculated array defectivity profile (trace "C") for a beam steering angle of 60 degrees, and FIG. 18C illustrates a comparison between experimental results (trace "E") and a calculated array defectivity profile (trace "C") for a beam steering angle of 120 degrees. As shown in each of FIGS. 18A-18C, the experimental results agreement well with the calculated array defectivity profile. Thus, an array as shown in FIG. 17 can be used to steer guided wave beams into any direction in the composite plate.

For some composite applications, guided wave energy can be focused in specific directions. In such applications, transducers 102 that excite guided waves with energy naturally focused to the desired directions are used. For composite materials with unknown material properties, multiple polar scans with different modes and frequencies may be applied to reduce effect of beam skewing, sidelobes, and to improve penetration power.

Figure 19:
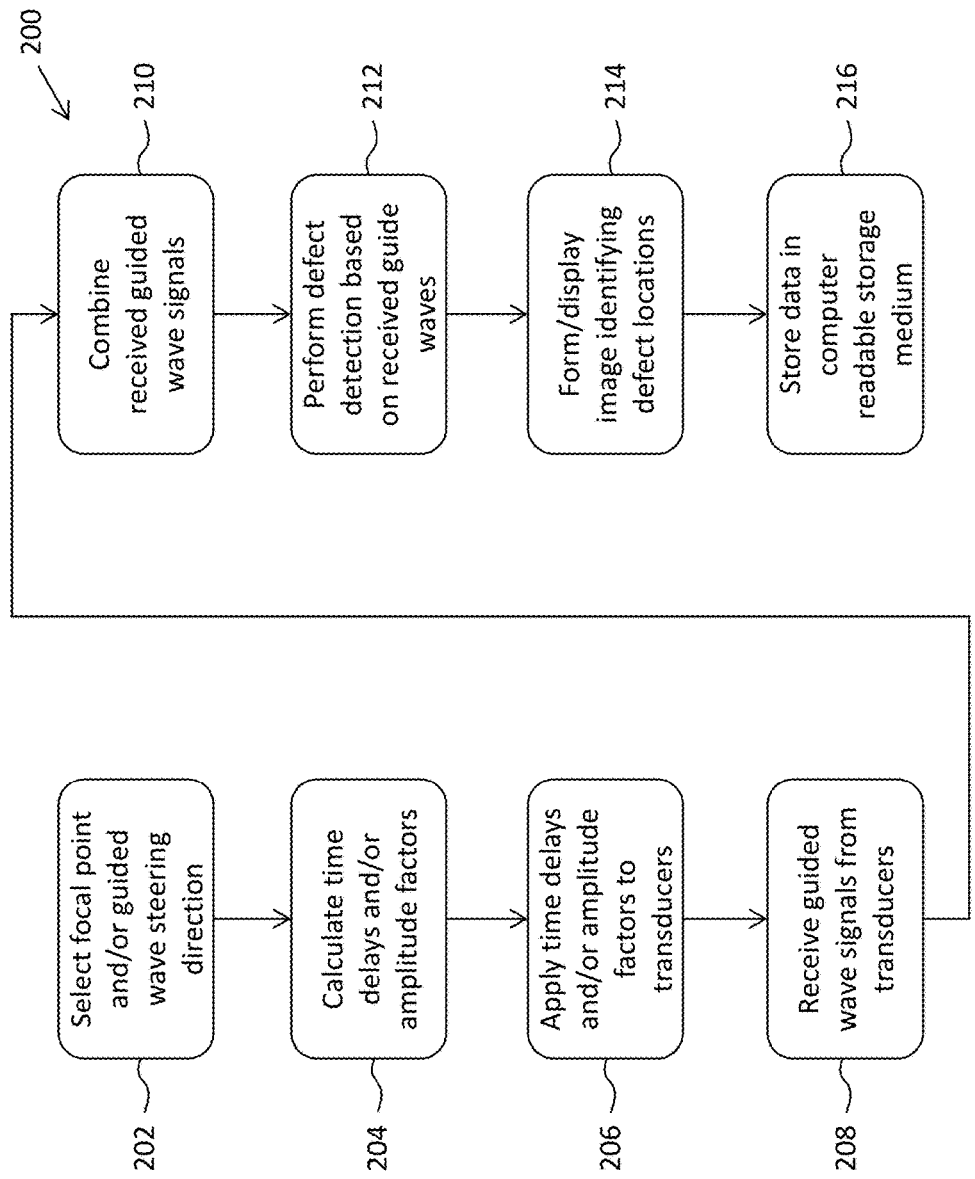
FIG. 19 is a flow diagram of one example of a method of performing structural health monitoring and/or non-destructive evaluation of plates and plate-like structures in accordance with some embodiments.

Turning now to FIG. 19, which is a flow diagram of one example of a method 200 of SHM/NDE of plates and plate-like structures using system 100, the operation and use of system 100 is described. At block 202, a focal point or guided wave beam steering direction on a plate or plate-like structure is selected. In some embodiments, for example, the focal point or guided wave beam steering direction is selected by a user. For example, a user can select a focal point or a guided wave beam steering direction to inspect a region of interest in the plate or plate-like structure. By changing the focal point or beam steering direction, method 200 can be repeated until a region of interest is completely inspected. In some embodiments, the selection of the guided wave beam steering direction is selected by system 100, which can be configured to automatically perform an inspection of the an entire region of interest by repeating method 200.

At block 204, time delays and/or possible amplitude factors are calculated. In some embodiments, system 100 calculates the time delays and/or amplitude factors and locations of the transducers. For example, time delays are applied to the array elements to achieve constructive interference in the beam steering direction for the purpose of beam steering. For example, FIG. 20A illustrates a wave path starting from an origin of a coordinate system as a reference. As shown in FIG. 20A, a time delay is used to compensate the phase difference from the wave generated by each element of the array. Letting $E_n$ denote the position of the nth transducer, $\vec{s}_n$ denote the position vector from the origin to the nth transducer, $\vec{\phi}$ be the unit vector pointing to the steering direction, and c represent the wave velocity, the time delay for compensating the phase difference for the nth element can be written as:

$$\Delta_n = -\frac{\vec{\phi} \cdot \vec{s}_n}{c}$$

Time delays are chosen to make the waves generated by all the transducers be focused at a focal point such that the waves arrive at the focal point at the same time. As illustrated in FIG. 20B, $\vec{r}_n$ is the vector pointing from the nth transducer to the focal point P, $\vec{r}$ and is the vector from the origin of the coordinate system to the focal point. The time delay for the nth array element can be calculated as:

$$\Delta_n = -\frac{|\vec{r}| - |\vec{r}_n|}{c}$$

At block 206, the calculated time delays and/or amplitude factors are applied to the array 103 of transducers 102 by controller 130. Transducers 102 are either fixedly connected and/or are disposed in a probe 105 that is placed in contact with a surface of a plate or plate-like structure. As described above, the plate or plate-like structure can be an anisotropic plate including, but not limited to, a multilayer fiber reinforced composite plate. In some embodiments, such as embodiments in accordance with the embodiment depicted in FIG. 9, additional transducers 102 other than those transducers 102 disposed in a probe 105 and/or provided in first array 103, are also placed on a surface of the plate or plate-like structure in an orderly arrangement or are placed randomly.

As described above, processor(s) 132 communicate with pulse generator 152 via communication infrastructure 134 causing pulse generator 152 to output control signals to transducers 102 in accordance with the time delays and/or amplitude factors. Transducers 102 cause one or more guided wave beams to propagate way from the array 103.

At block 208, reflections of the guided wave signals are received at one or more transducers 102 of array 103. In some embodiments, such as embodiments in accordance with the embodiment depicted in FIG. 9, additional transducers 102 other than those transducers 102 that generated the guided wave receive the reflected guide wave energy alone or in combination with the transmitting transducers 102. These additional transducers 102 can be disposed on the plate or plate-like structure in an orderly configuration or in a random configuration. The reflected signals received at transducers 102 are amplified by amplifier 154 and converted from an analog signal to a digital signal by A/D converter 156. The digital signal can be forwarded to processor(s) 132 via communication infrastructure 134 as will be understood by one of ordinary skill in the art.

At block 210, the received guided wave signals (e.g., reflected guided wave signals) are combined together. In some embodiments, the combination of the received signals is performed by processor(s) 132, which combine together the digital representation of the signals received from A/D converter 156 from communication infrastructure 134.

At block 212, the combined signals are used to perform defect detection by processor(s) 132. Possible defect reflections can be identified in the combined signals.

At block 214, an image of the plate or plate-like structure including an identification of a location of one or more defects is generated by processor(s) 132. In some embodiments, the generated image is displayed to a user on graphical interface/display 138, which receives signals from processor(s) 132 via display interface 136.

At block 216, the inspection data (e.g., defect location data and/or graphical representation data) are stored in a non-transient computer readable storage medium. For example, the data can be stored in main memory 140 and/or secondary memory 142 in response to processor(s) 132 transmitting the data via communication infrastructure 134.

Figure 21A:
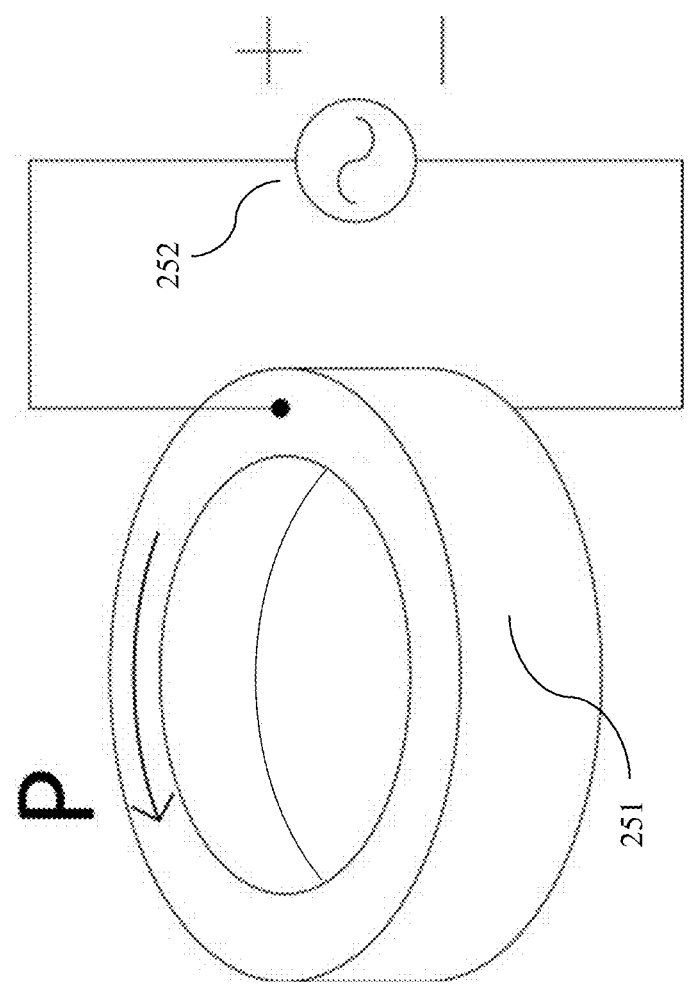
FIG. 21A illustrates one example of a circumferentially shear polarized $d_{15}$ piezoelectric ring transducer in accordance with some embodiments.
Figure 21B:
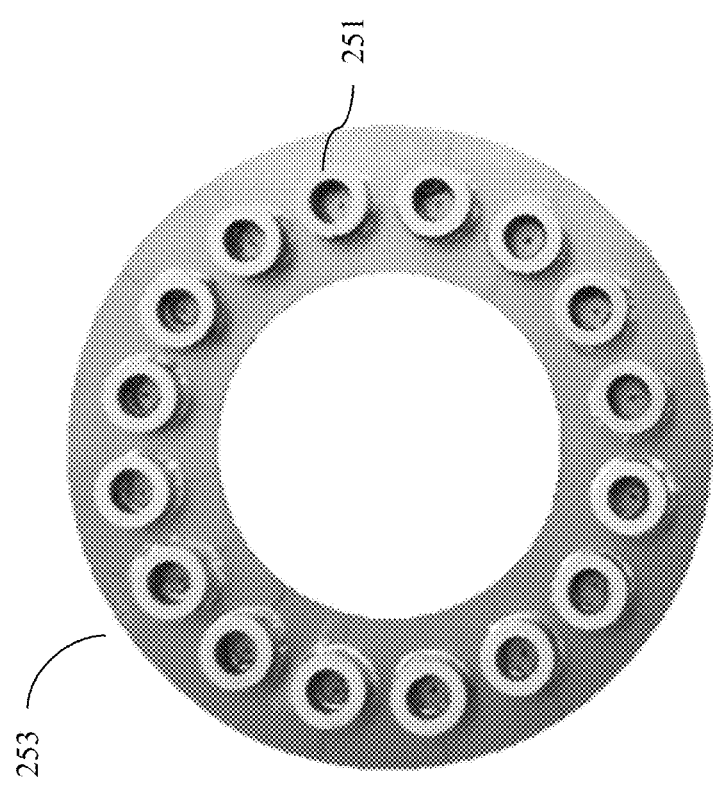
FIG. 21B illustrates one embodiment wherein 16 circumferentially polarized shear rings are arranged into a circular array for damage detection in plate-like structures.

FIG. 21A discloses one example of a circumferentially shear polarized $d_{15}$ piezoelectric ring element in accordance with some embodiments. When pulsed with one or more AC voltages from an AC voltage source 252, circumferentially poled ring-type actuator 251 excites shear horizontal (SH)-type guided waves in plate-like structures using the $d_{15}$ piezoelectric mode. SH waves are not sensitive to liquid loading conditions that are frequently encountered in tank floor monitoring applications. Additionally, the fundamental SH wave mode, the $SH_0$ mode, is non-dispersive in isotropic structures such as steel plates. These circumferentially polarized shear elements oscillate in a torsional mode, which yields omnidirectional SH wave generation and reception. Analytical calculations, numerical finite element simulations, and/or experimental tests can be used to determine the dimensions of the piezoelectric ring transducers 251 for different applications, and are within the abilities of one of ordinary skill in the art. One example of a circular 16-element phased array 253 comprising a plurality of poled ring-type actuators 251 is illustrated in FIG. 21B.

In some embodiments, a structural health monitoring approach is adopted, in which guided wave imaging results and guided wave signals can be compared from data sets collected at different times. This approach improves defect sensitivity by removing pre-existing features such as welds, stiffeners, rivets, access ports, and other discontinuities from the image as only changes in the imaging results are considered. This approach is particularly advantageous for monitoring the growth of defects over time. In some embodiments, a fixture is applied to a structure to achieve consistent probe positioning and coupling.

Figures 1, 22C:
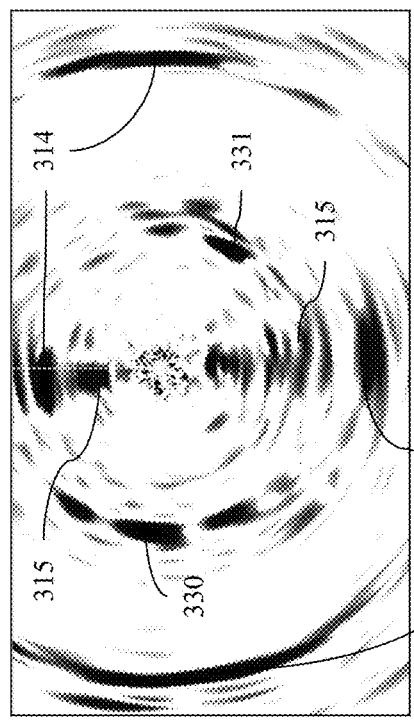
Figures 2, 22C:
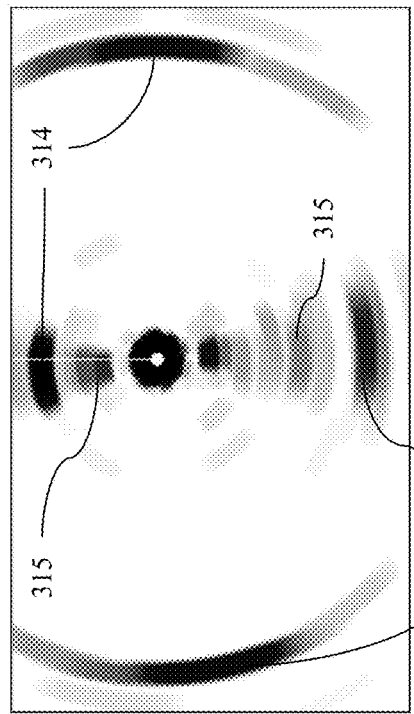
Figures 3, 22C:
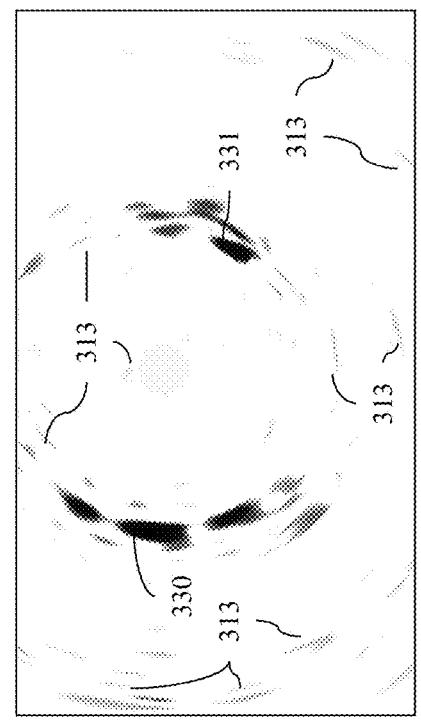
Figures 4, 22C:
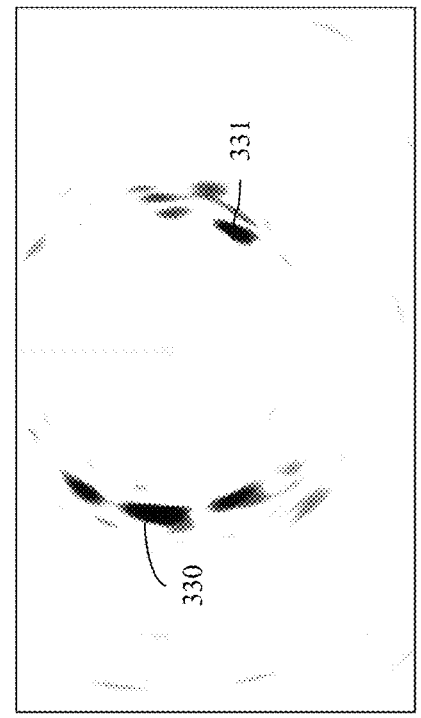

In some embodiments, the SHM approach is realized by subtracting the image associated with a first state from the image associated with a second state. One example of this baseline subtraction approach is illustrated in FIGS. 22A-1-22A-4. For example, FIG. 22A-1 shows a 16-element phased array shear ring probe 253 disposed on a steel plate structure 254 with welded steel stiffeners 257 before and after corrosion simulation defects 255 and 256 were introduced. During the SHM processing of this data, the image in FIG. 22A-2, which is associated with a defect-free state, is subtracted, point-by-point, from the image in FIG. 22A-3, which is associated with a state in which corrosion defects have been introduced to the structure. The resulting image shown in FIG. 22A-4 includes a reduced amplitude of many of the static features, such as plate edges 304 and stiffeners 305, with features 330 and 331 in FIGS. 22A-3 and 22A-4 corresponding to defects 255 and 256 in FIG. 22A-1. The reduction in amplitudes of these static features advantageously improves the image quality and ease of interpretation.

In some embodiments, additional SHM processing can be applied to further reduce the amplitude of static features by applying a suppression algorithm to the two data sets. Due to natural variations in the amplitude of the reflections from various features in a structure, the static features are often not completely removed from the SHM image by the baseline subtraction algorithm. For example, edge reflections 304 and stiffener reflections 305 in FIGS. 22A-2 and 22A-3, respectively, are not fully removed in the image shown in FIG. 22A-4 after baseline subtraction and appear as 304-1 and 305-1, respectively, in FIG. 22A-4. These variations in reflection amplitudes can occur due to temperature variations, boundary condition changes, coupling variations, probe inconsistencies, and other variations that cannot be eliminated.

In some embodiments, the suppression algorithm divides a baseline subtraction SHM image point-by-point by an amplified version of a baseline image to produce a suppressed SHM image which greatly reduces or eliminates the static reflectors to yield a clearer image of defects. For example, FIG. 22B-1 provides an image, identical to that of FIG. 22A-3 of the reflections generated by the discontinuities in the plate shown in FIG. 22A-1. FIG. 22B-2 illustrates the amplified version of the baseline image shown in FIG. 22A-2, which is subtracted from the image in FIG. 22B-1 to produce a clearer image of defects 330, 331 as shown in FIG. 22B-3 as compared to the baseline-subtraction image shown in FIG. 22A-4. The amplification of the baseline divisor, FIG. 22B-2, can be adjusted to suit the needs of the structure and the data.

In additional embodiments, a stretch suppression algorithm is applied in which the spatial region of influence of each reflector is extended in at least one dimension to account for minor misalignments of the static reflectors between the baseline and second images. FIGS. 22C-1-22C-4 illustrate one example of this concept. For example, the original baseline image shown in FIG. 22A-2 is stretched and amplified to generate the suppression image illustrated in FIG. 22C-2. The defect image shown in FIG. 22C-1 is then divided by the stretched and amplified baseline image shown in FIG. 22C-2 to obtain the stretch-suppressed SHM image shown in FIG. 22C-4. The stretch-suppressed SHM image shown in FIG. 22C-4 exhibits a further reduction of static reflections 314 and 315 compared to SHM image shown in FIG. 22C-3, which was developed with an un-stretched suppression algorithm and contains artifacts 313. Corrosion defect reflections 330 and 331 become more apparent after stretch suppression. The degree to which each reflector is extended during stretch suppression can be adjusted to suit the needs of the structure and the data.

An image realignment algorithm may also be applied which compensates for minor misalignment of the probe by adjusting the baseline and second images before applying the SHM routines. This alignment can, in some embodiments, be accomplished by calculating the two-dimensional cross-correlation of the baseline and second images and subsequently offsetting the second image in accordance with the offset required to maximize the cross-correlation value. This process aligns the static features that are common between the two images.

Figures 2, 23A:
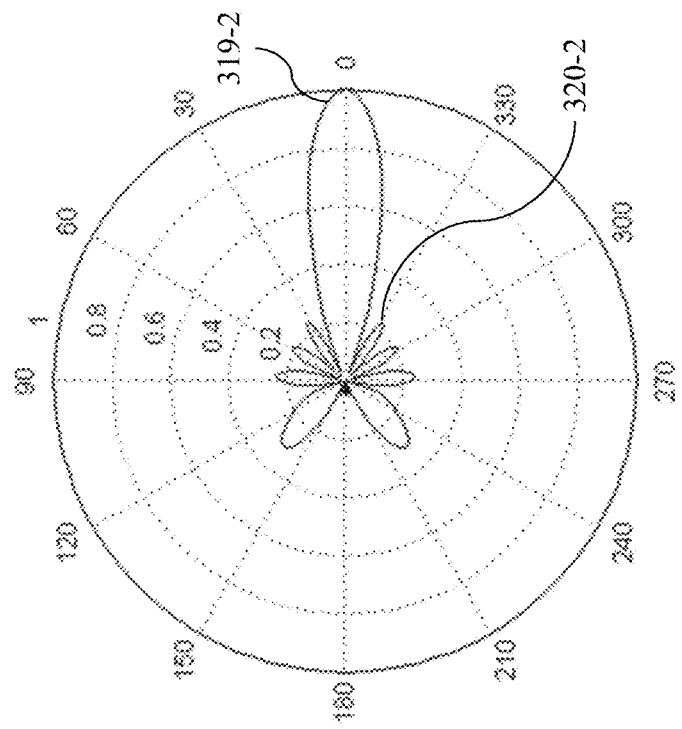
Figures 1, 23A:
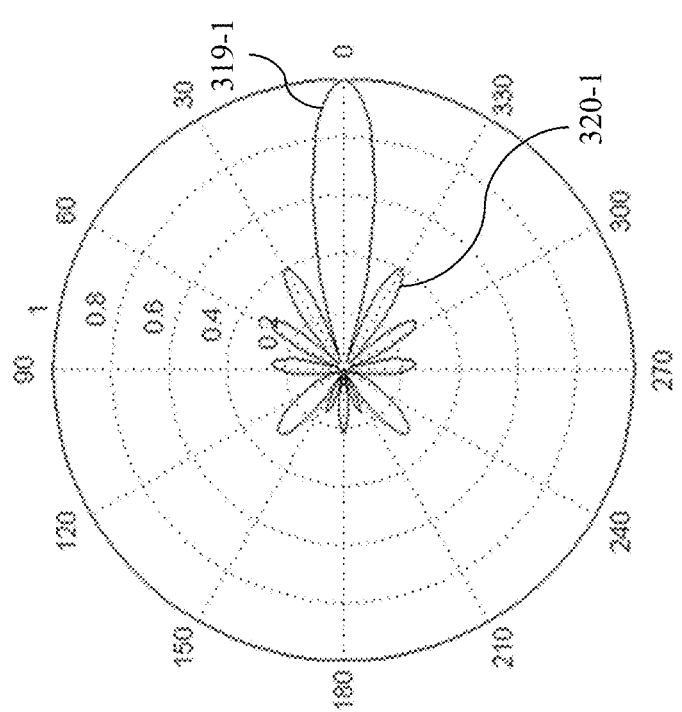

Amplitude scaling factors may be applied to the excitation signals applied across the terminals of the one or more transducer elements in order to reduce the amplitude of the sidelobes of beam directivity profiles during phased array focusing. For example, FIG. 23A-1 is the beam directivity profile of a particular array without apodization, and FIG. 23A-2 is the beam directivity profile of the same array with Hamming apodization. This method, known as apodization, can be applied using various windowing functions including, but not limited to, a Hann window, a Hamming window, a Blackman-Harris window, a flat-top window, and customized versions of one of these windows. As shown in FIGS. 23A-1 and 23A-2, the side lobes 320-2 in FIG. 23A-2 are smaller than the side lobes 320-1 in FIG. 23A-1. However, the main beam lobe 319-2 in FIG. 23A-2 is wider than the main beam lobe 319-1 in FIG. 23A-1.

Figures 2, 23B:
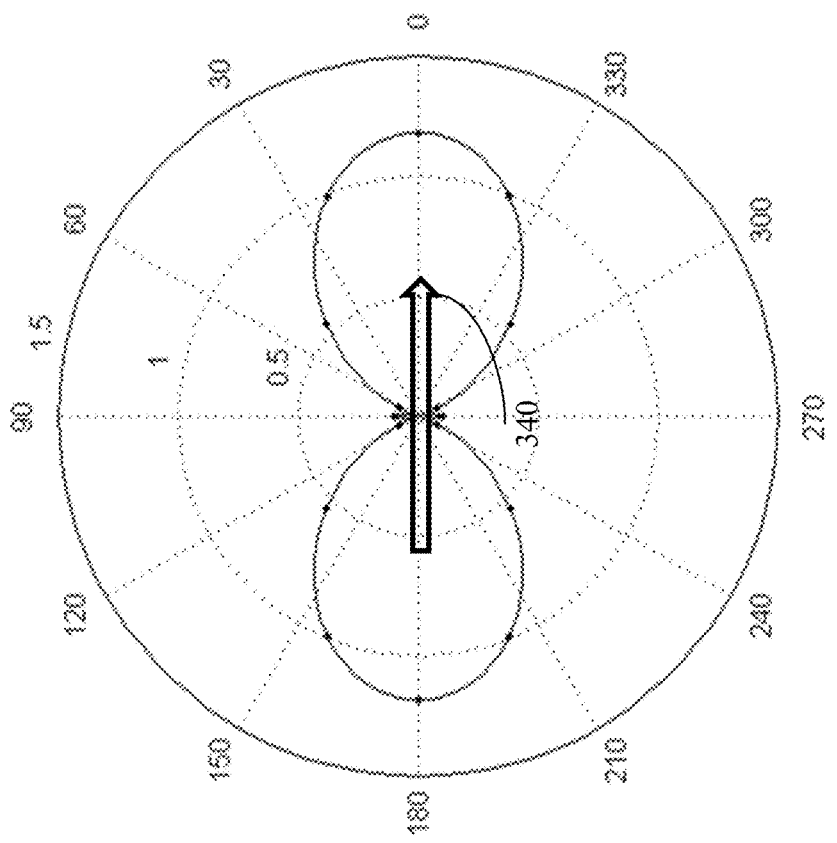
Figures 1, 23B:
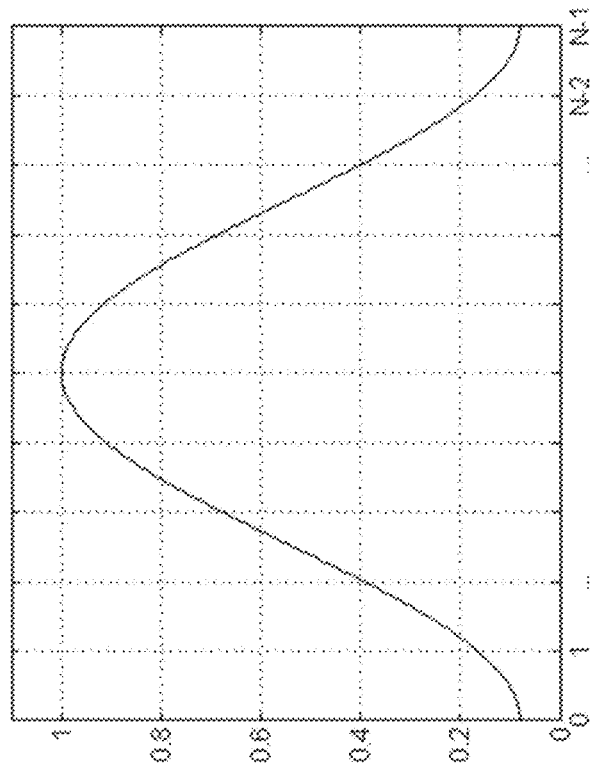
Figures 2, 23C:
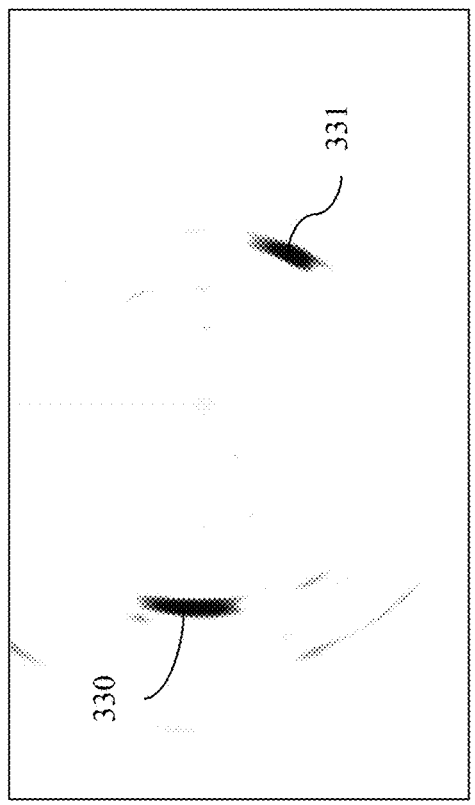
Figures 1, 23C:
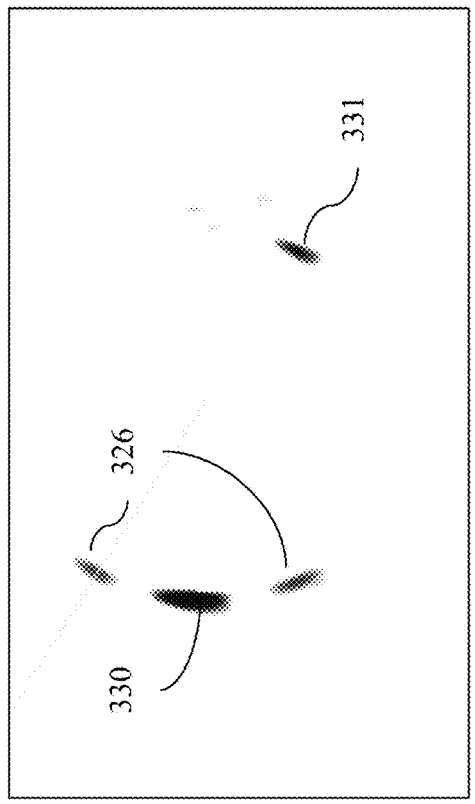

FIG. 23B-1 illustrates a Hamming window function in general terms, and FIG. 23B-2 illustrates a Hamming window function as applied to a circular phased array for steering direction 340. Similar apodization can be applied to the guided wave signals during post-processing. For example, FIG. 23C-1 illustrates a SHM phased array image of the steel plate structure 254 with welded steel stiffeners 257 illustrated in FIG. 22A-1 without apodization, and FIG. 23C-2 illustrates the same image with apodization. Note that the amplitude of the sidelobes 326 is reduced with respect to the amplitude of the main beam reflection 330 from the corrosion defect. For the case of a Hamming window apodization function $A(n,\phi)$, the relative amplitudes of the various elements of a circular array can be calculated by applying the following equation:

$$A(n,\phi)=\alpha-(1-\alpha)\cos[\pi+2(\psi_n-\phi)]$$

where n is the array element number, $\phi$ is the beam steering or focusing angle, $\psi_n$ is the angular position of array element n, and $\alpha$ is a factor between 0.5 and 1.

One or more calibration targets may be affixed to the plate-like structure being inspected to act as references for NDE and SHM embodiments of the system. In some embodiment, for NDE, the one or more calibration targets can be used to measure guided wave velocity in the material, to perform a transducer and system self-check, and to achieve defect sizing. Since the dimensions and reflection characteristics of the one or more calibration targets are known, the guided wave reflections from the one or more targets can be compared to the reflections from defects in the structure to calculate the size of the defects. Several non-limiting embodiments of the calibration target include a metallic or polymer rod or block.

Figure 24:
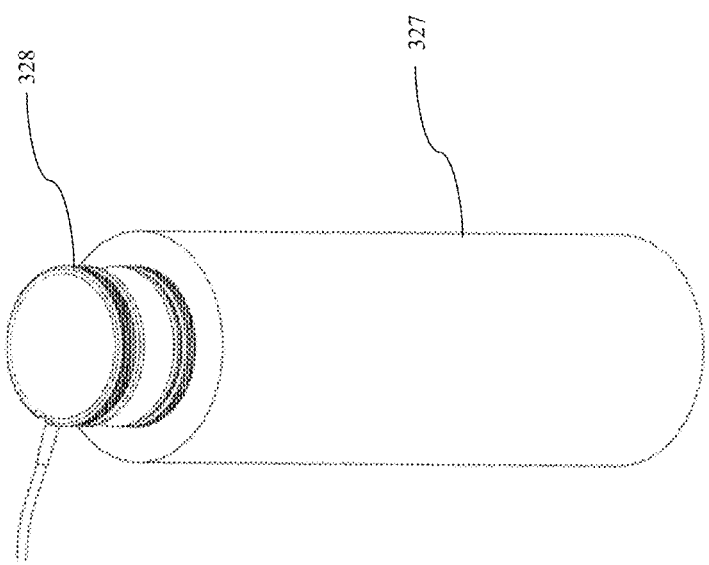
FIG. 24 illustrates one example of a transducer calibration rod.

Additional calibration of the guided wave probe can be conducted separately from the structure by coupling the probe to a calibration plate or rod, such as the example of a Plexiglas cylinder 327 illustrated in FIG. 24 for the purposes of calibrating probe 328. Pulse-echo and pitch-catch measurements may be collected by each transducer element and compared to evaluate the health of each element and to calibrate the relative sensitivity of each element prior to data collection. Imbalances in the sensitivity of various elements in the guided wave phased array can lead to undesirable image artifacts and incorrect focusing. In some embodiments, the element calibration plate or rod is constructed of a material such as Plexiglas, which has a low wave velocity, in order to reduce the dimensions of the calibration specimen.

The disclosed systems and methods described above advantageously enable SHM/NDE of plates and plate-like structures using guided wave phased arrays. The plates or plate-like structures can be anisotropic materials, including multilayer fiber reinforced composite materials, and can be dry or under water/liquid loading conditions. The transducers of the disclosed systems can be individually or simultaneously excited and can be placed closely together on the structure to form a compact array and/or distributed on the structure at some distance away from each other in a random or orderly configuration. In some embodiments, the transducers include shear $d_{15}$ PZT type transducers for generating and receiving SH-type guided waves for applications on structures subject to water loading conditions. The disclosed systems use a number of pulser and receiver channels into which time delays can be input.

Additionally the disclosed systems can be used to perform real-time phased array beam steering and/or focusing utilizing guided wave transducers with mode and frequency selection capability for guided wave phased array and/or CT testing. Physically based guided wave features can be extracted from guided wave signals for damage detection and evaluation.

In some embodiments, the systems are configured to perform guided wave phased array tests or guided wave CT tests individually. In some embodiments, the systems also are configured to combine the guided wave phased array approach with the guided wave CT approach.

The disclosed systems and methods can be at least partially embodied in the form of program code embodied in tangible media, such as floppy diskettes, CD-ROMs, DVD-ROMs, Blu-ray disks, hard drives, or any other tangible and non-transient machine-readable storage medium, wherein, when the program code is loaded into and executed by a machine, such as a computer, the machine becomes an apparatus for practicing the method. The disclosed systems and methods can also be embodied, at least partially, in the form of program code, for example, whether stored in a storage medium, loaded into and/or executed by a machine, or transmitted over some transmission medium, such as over electrical wiring or cabling, through fiber optics, or via electromagnetic radiation, wherein, when the program code is loaded into and executed by a machine, such as a computer, the machine becomes an apparatus for practicing the methods. When implemented on a general-purpose processor, the program code segments combine with the processor to provide a unique device that operates analogously to specific logic circuits.

Although the disclosed systems and methods have been described in terms of exemplary embodiments they are not limited thereto. Rather, the appended claims should be construed broadly, to include other variants and embodiments of the disclosed systems and methods, which may be made by those skilled in the art without departing from the scope and range of equivalents of the systems and methods.

What is claimed is:

1. An ultrasonic guided wave system, comprising:
at least two guided wave transducers configured to be disposed on a structure, at least a first one of the at least two guided wave transducers configured to transmit shear horizontal guided wave energy in the structure in response to oscillating in a torsional mode, and at least a second one of the at least two guided wave transducers configured to detect shear horizontal guided wave energy in the structure; and
a controller communicatively coupled to the at least two guided wave transducers, the controller including a processor configured to
cause the at least one of the at least two guided wave transducers to be pulsed such that shear guided wave energy is steered in a predetermined direction in the structure or is focused at a predetermined focal point, and
process at least one reflected guided wave signal to identify a location of at least one possible defect in said structure, and
wherein at least one of the at least two transducers is a circumferentially shear polarized $d_{15}$ piezoelectric ring transducer.

2. The ultrasonic guided wave system of claim 1, wherein the at least two transducers are coupled to a housing to form a portable multi-transducer probe.

3. The ultrasonic guided wave system of claim 1, wherein at least one of the at least two transducers is a magnetostrictive transducer.

4. An ultrasonic guided wave system, comprising:
a plurality of guided wave transducers, at least one first set of the plurality of guided wave transducers including circumferentially shear polarized ring-shaped $d_{15}$ piezoelectric transducers configured to oscillate in a torsional mode to omnidirectionally transmit shear horizontal guided wave energy in a structure; and
a controller communicatively coupled to the plurality of guided wave transducers, the controller including a processor configured to
cause the at least one first set of the plurality of guided wave transducers to be sequentially pulsed to generate a plurality of shear horizontal guided waves in the structure,
apply a back-propagation algorithm to received guided wave signals that are received from the structure at a second set of the plurality of guided wave transducers, and
identify a location of at least one possible defect in the structure based on the received guided wave signals.

5. The ultrasonic guided wave system of claim 4, wherein the plurality of guided wave transducers are coupled to a housing to form a portable multi-transducer probe.

6. The ultrasonic guided wave system of claim 4, wherein at least one of the plurality of guided wave transducers is a magnetostrictive transducer.

7. A method, comprising:
a) driving at least a first one of a plurality of transducers in a torsional mode to cause omnidirectional shear horizontal guided waves to be transmitted in a structure;
b) receiving, by at least a second one of the plurality of transducers, at least one reflected guided wave signal; and
c) processing the at least one reflected guided wave signal to identify a location of at least one possible defect in the structure, and
wherein the at least first one of the plurality of transducers is a circumferentially shear polarized $d_{15}$ piezoelectric transducer having a ring shape.

8. A method, comprising:
a) driving at least a first one of a plurality of transducers in a torsional mode to cause shear horizontal guided waves to be transmitted in a structure;
b) receiving, by at least a second one of the plurality of transducers, at least one reflected guided wave signal;
c) processing the at least one reflected guided wave signal to identify a location of at least one possible defect in the structure,
wherein the at least first one of the plurality of transducers is a circumferentially shear polarized $d_{15}$ piezoelectric transducer having a ring shape, and
wherein step a) includes:
determining at least one of a direction in which the shear horizontal guided waves are to be transmitted in the structure or a focal point at which the shear horizontal guided waves are to be focused;
calculating at least one of a time delay and an amplitude for a control signal for driving at least one of the plurality of transducers; and
driving said plurality of transducers in accordance with the time delay or the amplitude such that guided wave energy is steered in the direction in the structure or is focused at the focal point.

9. The method of claim 8, further comprising repeating steps a), b), and c) for at least one of different predetermined directions and predetermined locations.

10. The method of claim 7, wherein a plurality of reflected guided wave signals are received, and step c) includes combining the reflected guided wave signals using back propagation signal synthesis.

11. The method of claim 7, further comprising:
d) generating processed image data by performing at least one of baseline image subtraction and image suppression on image data of the structure.

12. The method of claim 11, wherein performing baseline image subtraction includes subtracting first image data acquired at a first point in time from second image data acquired at a second point in time.

13. The method of claim 11, further comprising:
e) coupling at least one calibration target to the structure; and
f) using the at least one calibration target as a reference for the purposes of at least one of system calibration, defect sizing, velocity calculations, and compensation for environmental variation.

14. The method of claim 11, wherein image suppression includes applying a suppression algorithm to the processed image data to reduce the amplitude of indications from pre-existing reflectors that arise due to variations in the reflected signals from said structural reflectors between a baseline data set and a secondary data set.

15. The method of claim 11, wherein image suppression includes applying an image realignment algorithm to compensate for variations in a position from which at least one of the plurality of transducers is coupled to the structure.

16. The method of claim 11, further comprising using a calibration rod to adjust a relative sensitivity of the plurality of transducers to improve a balance of the transmitted and received guided wave signals.

* * * * *